Figure 1C:
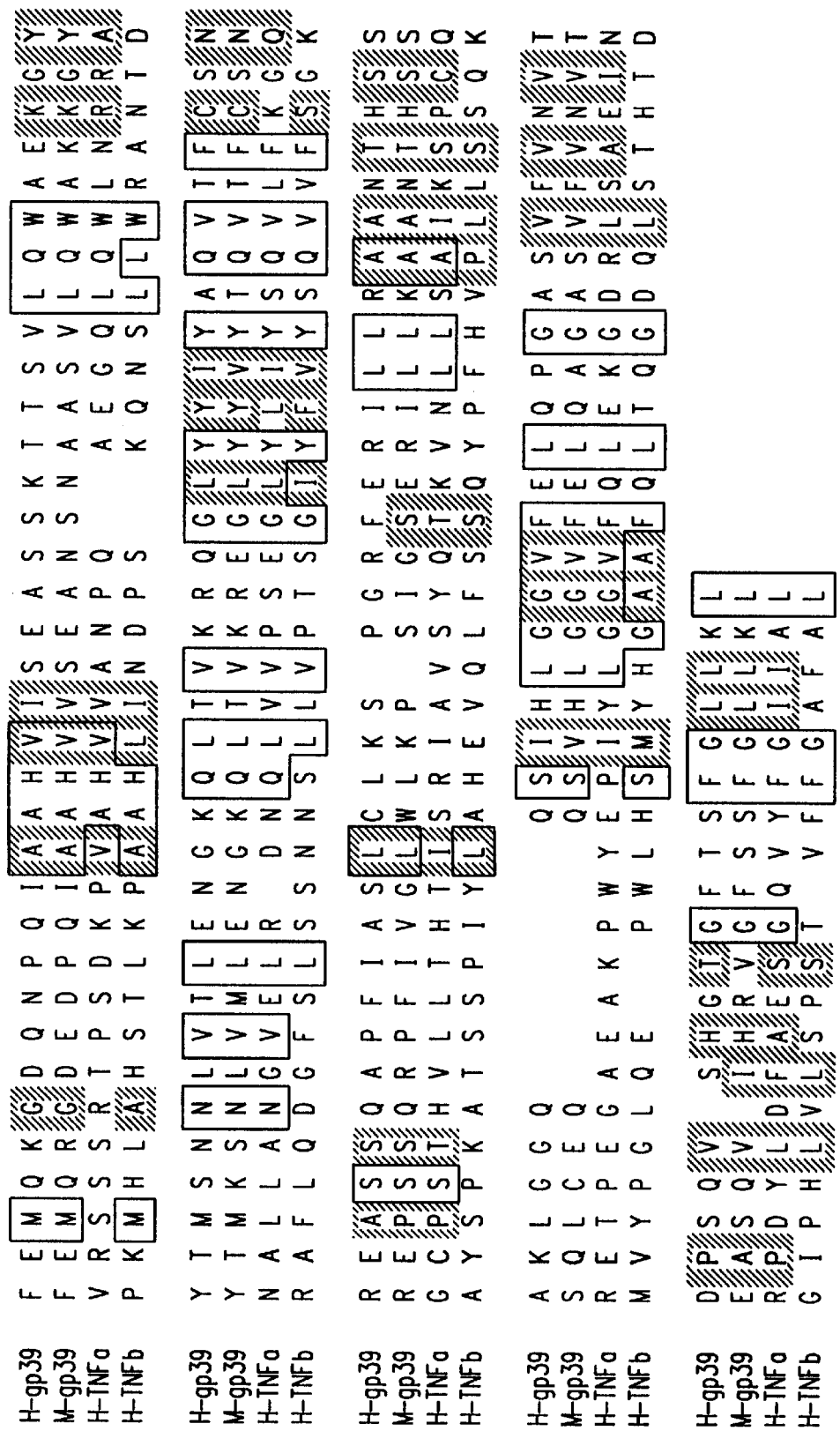

United States Patent [19]
Aruffo et al.

[11] Patent Number: 5,945,513
[45] Date of Patent: Aug. 31, 1999

[54] FUSION PROTEINS COMPRISING GP39 AND CD8

[75] Inventors: Alejandro Aruffo, Edmonds; Diane Hollenbaugh; Jeffrey A. Ledbetter, both of Seattle, all of Wash.

[73] Assignee: Bristol-Myers Squibb, Seattle, Wash.

[21] Appl. No.: 08/690,096

[22] Filed: Jul. 30, 1996

Related U.S. Application Data

[62] Division of application No. 07/940,605, Sep. 4, 1992, Pat. No. 5,540,926.

[51] Int. Cl.$^6$ .................................................... C07K 19/00
[52] U.S. Cl. ............................... 530/387.3; 424/134.1; 424/192.1; 435/69.7; 435/471; 530/350
[58] Field of Search ........................... 536/23.5; 530/350, 530/387.1; 935/10; 544/2, 8, 12; 424/134.1; 435/69.1, 320.1

[56] References Cited

U.S. PATENT DOCUMENTS

| | | |
|---|---|---|
| 5,116,964 | 5/1992 | Capon et al. . |
| 5,474,771 | 12/1995 | Lederman et al. .................... 424/133.1 |
| 5,540,926 | 7/1996 | Aruffo et al. . |
| 5,565,321 | 10/1996 | Spriggs et al. ............................ 435/6 |
| 5,567,611 | 10/1996 | Ralph et al. . |

FOREIGN PATENT DOCUMENTS

| | | |
|---|---|---|
| 0 330 191 | 2/1989 | European Pat. Off. . |
| 0 555 880 | 8/1993 | European Pat. Off. . |
| 93/08207 | 4/1993 | WIPO . |
| 93/09812 | 5/1993 | WIPO . |
| 94/04570 | 3/1994 | WIPO . |

OTHER PUBLICATIONS

Hollenbaugh et al. Current Opinion in Immunology 4:216–219 (1992).
Hollenbaugh et al. Current Photococs in Immunology Unit 10.19 (1992).
Paterson et al. J Cell Biology 110: 999–1011 (1990).
Armitage et al., 1992, Nature, 357:80–82.
Gray et al., 1984, Nature, 312:721–724.
Hollenbaugh et al., 1992, EMBO J., 11(12):4313–4321.
Lederman et al., 1992, J. Exper. Med., 175(4):1091–1101.
Noelle et al., 1992, Proc. Natl. Aca. Sci. USA, 89:6550–6554.
Noelle et al., 1992, Current Opinion Immunology, 4(3):333–337.
Pennica et al., 1984, Nature, 312:724–729.
Wang et al., 1985, Science, 228:149–154.
Spriggs et al., J.Exp.Med. 176:1543–1550, Dec. 1, 1992.
Graf et al., Eur. J. Immunol. 22:3191–3194, Dec. 1992.
Gauchat et al., FEBS Lett. 315:259–266, Jan. 1993.
Lazar et al, Mol.Cell.Biol. 8:1247–1252, Mar. 1988.

Primary Examiner—Christina Y. Chan
Assistant Examiner—Phillip Gambel
Attorney, Agent, or Firm—Pennie & Edmonds llp

[57] ABSTRACT

The present invention relates to fusion proteins having gp39 protein sequences, which fusion proteins bind to the B cell antigen, CD40. More specifically, the invention relates to fusion proteins having gp39 protein sequences attached to a polypeptide having an amino terminal secretory signal sequence to allow export of the fusion protein out of the recombinant host cell in which it is produced. The fusion proteins of this invention may be useful for promoting B cell proliferation.

2 Claims, 11 Drawing Sheets

```
1    CCATTTCAACTTTAAACACAGCATGATCGAAACATACAACCAAACTTCTCCC
1                     MetIleGluThrTyrAsnGlnThrSerPro
                                       ---CHO---

52   CGATCTGCGGCCACTGGACTGCCCATCAGCATGAAAATTTTATGTATTACTT
11   ArgSerAlaAlaThrGlyLeuProIleSerMetLysIlePheMetTyrLeuLeu

106  ACTGTTTTCTTATCACCCAGATGATTGGGTCAGCACTTTTGCTGTGTATCTT
29   ThrValPheLeuIleThrGlnMetIleGlySerAlaLeuPheAlaValTyrLeu
                           TM

160  CATAGAAGGTTGGACAAGATAGAAGATGAAAGGAATCTTCATGAAGATTTGTA
47   HisArgArgLeuAspLysIleGluAspGluArgAsnLeuHisGluAspPheVal

214  TTCATGAAAACGATACAGAGATGCAACACAGGAGAAAGATCCTTATCCTTACTG
65   PheMetLysThrIleGlnArgCysAsnThrGlyGluArgSerLeuSerLeuLeu

268  AACTGTGAGGAGATTAAAAGCCAGTTTGAAGGCTTTGTGAAGGATATAATGTTA
83   AsnCysGluGluIleLysSerGlnPheGluGlyPheValLysAspIleMetLeu

322  AACAAAGAGGAGAAGAAGAAAAACAGCTTTGAAATGCAAAAGGTGATCAG
101  AsnLysGluThrLysLysGluAsnSerPheGluMetGlnLysGlyAspGln

376  AATCCTCAAATTGCGGCACATGTCATAAGTGAGGCCAGCAGTAAAACAACATCT
119  AsnProGlnIleAlaAlaHisValIleSerGluAlaSerSerLysThrThrSer
```

FIG. 1A

```
430  GTGTTACAGTGGGCTGAAAAGGATACTACACCATGAGCAACAACTTGGTAACC
137  ValLeuGlnTrpAlaGluLysGlyTyrTyrThrMetSerAsnAsnLeuValThr

484  CTGGAAAATGGGAAACAGCTGACCGTTAAAGACAAGGACTCTATTATATCTAT
155  LeuGluAsnGlyLysGlnLeuThrValLysArgGlnGlyLeuTyrTyrIleTyr

538  GCCCAAGTCACCTTCTGTTCCAATCGGGAAGCTTCGAGTCAAGCTCCATTATA
173  AlaGlnValThrPheCysSerAsnArgGluAlaSerSerGlnAlaProPheIle

592  GCCAGCCTCTGCCTAAAGTCCCCCGGTAGATTCGAGAGAATCTTACTCAGAGCT
191  AlaSerLeuCysLeuLysSerProGlyArgPheGluArgIleLeuLeuArgAla

646  GCAAATACCCACAGTTCCGCCAAACCTTGCGGGCAACAATCCATTCACTTGGA
209  AlaAsnThrHisSerSerAlaLysProCysGlyGlnSerIleHisLeuGly

700  GGAGTATTTGAATTGCAACCAGGTGCTTCGGTTGTGTTTGTCAATGTGACTGATCCA
227  GlyValPheGluLeuGlnProGlyAlaSerValPheValAlaSerValThrAspPro
                                              ---CHO---

754  AGCCAAGTGAGCCATGGCCACTGGCTTCACGTCCTTTGGCTTACTCAAACTCTGA
245  SerGlnValSerHisGlyThrGlyPheThrSerPheGlyLeuLeuLysLeuEnd

808  ACAGTGTCACCTTGCAGGCTGTGGTGGAGCTGA
```

FIG. 1B

FIG.3A
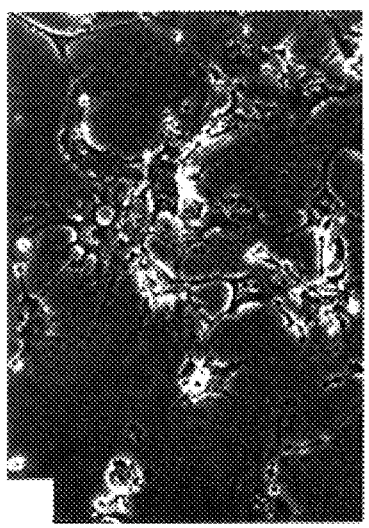
FIG.3C
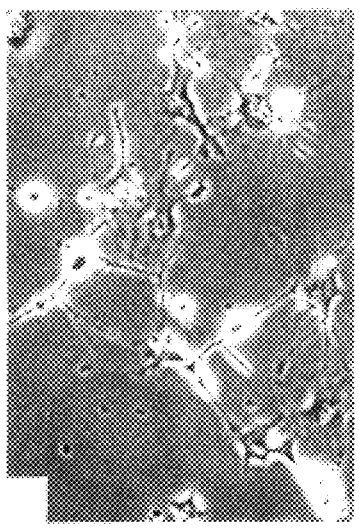
FIG.3E
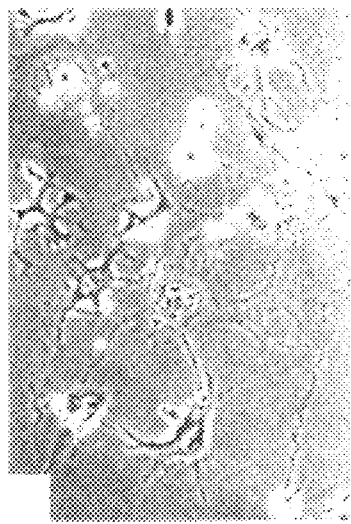
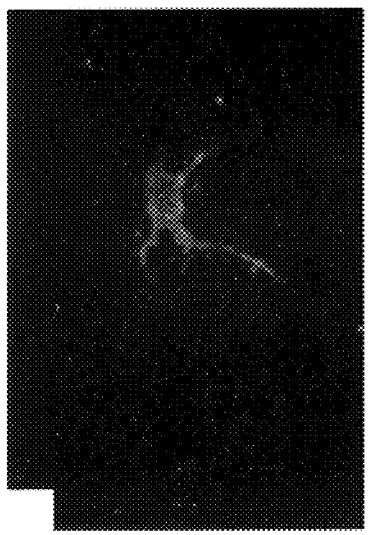
FIG.3B
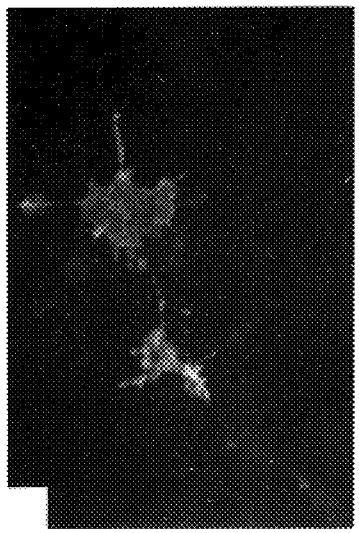
FIG.3D
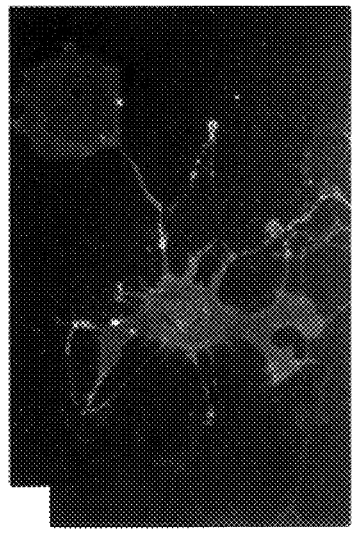
FIG.3F

```
   1  GCTGGCTAAA  GGAGCAGTTT  CCCGACCCT   ACACGCCTCC  CCCACCGCAC
  51  CTCCTCCGCC  CTGTTCCTGG  GCCCCTCCCC  TAGAGCCCTA  GCTTGACCTA
 101  AGCTGCTTGC  TGGTGGAGAG  CACACCATGG  CCTCACCGTT  GACCCGCTTT
 151  CTGTCGCTGA  ACCTGCTGCT  GCTGGGTGAG  TCGATTATCC  TGGGGAGTGG
 201  AGAAGCTAAG  CCACAGGCAC  CCGAACTCCG  AATCTTTCCA  AAGAAAATGG
 251  ACGCCGAACT  TGGTCAGAAG  GTGGACCTGG  TATGTGAAGT  GTTGGGGTCC
 301  GTTTCGCAAG  GATGCTCTTG  GCTCTTCCAG  AACTCCAGCT  CCAAACTCCC
 351  CCAGCCCACC  TTCGTTGTCT  ATATGGCTTC  ATCCCACAAC  AAGATAACGT
 401  GGGACGAGAA  GCTGAATTCG  TCGAAACTGT  TTTCTGCCAT  GAGGGACACG
 451  AATAATAAGT  ACGTTCTCAC  CCTGAACAAG  TTCAGCAAGG  AAAACGAAGG
 501  CTACTATTTC  TGCTCAGTCA  TCAGCAACTC  GGTGATGTAC  TTCAGTTCTG
 551  TCGTGCCAGT  CCTTCAGAAA  GTGAACTCTA  CTACTACCAA  GCCAGTGCTG
 601  CGAACTCCCT  CACCTGTGCA  CCCTACCGGG  ACATCTCAGC  CCCAGAGACC
 651  AGAAGATTGT  CGGCCCCGTG  GCTCAGTGAA  GGGGACCGGA  TTGGACTTCG
 701  CCTGTGATAT  TTACATCTGG  GCACCCCTTG  CCGGAATCTG  CGTGGCCCTT
 751  CTGCTGTCCT  TGATCATCAC  TCTCATCTGC  TACCACAGGA  GCCGAAAGCG
 801  TGTTTGCAAA  TGTCCCAGGC  CGCTAGTCAG  ACAGGAAGGC  AAGCCCAGAC
 851  CTTCAGAGAA  AATTGTGTAA  AATGGCACCG  CCAGAAGCTT  ACAACTACTA
 901  CATGACTTCA  GAGATCTCTT  CTTGCAAGAG  GCCAGGCCCT  CCTTTTTCAA
 951  GTTTCCTGCT  GTCTTATGTA  TT

1  MASPLTRFLS  LNLLLLGESI  ILGSGEAKPQ  APELRIFPKK  MDAELGQKVD
  51  LVCEVLGSVS  QGCSWLFQNS  SSKLPQPTFV  VYMASSHNKI  TWDEKLNSSK
 101  LFSAMRDTNN  KYVLTLNKFS  KENEGYYFCS  VISNSVMYFS  SVVPVLQKVN
 151  STTKPVLRT   PSPVHPTGTS  QPQRPEDCRP  RGSVKGTGLD  FACDIYIWAP
 201  LAGICVALLL  SLIITLICYH  RSRKRVCKCP  RPLVRQEGKP  RPSEKIV*NG
```

FIG. 8

```
   1 CGGCTCCCGC GCCGCCTCCC CTCGCGCCCG AGCTTCGAGC CAAGCAGCGT
  51 CCTGGGGAGC GCGTCATGGC CTTACCAGTG ACCGCCCTTGC TCCTGCCGCT
 101 GGCCTTGCTG CTCCACGCCG CCAGGCCGAG CCAGTTCCGG GTGTCGCCGC
 151 TGGATCGGAC CTGGAACCTG GGCGAGACAG TGGAGCTGAA GTGCCAGGTG
 201 CTGCTGTCCA ACCCGACGTC GGGCTGCTCG TGGCTCTTCC AGCCGCGCGG
 251 CGCCCGCCGC AGTCCCCACCT TCCTCCCTATA CCTCTCCCAA AACAAGCCCA
 301 AGGCGGCCGA GGGGCTGGAC ACCCAGCGGT TCTCGGGCAA GAGGTTGGGG
 351 GACACCTTCG TCCTCACCCT GAGCGACTTC CGCCGAGAGA ACGAGGGCTA
 401 CTATTTCTGC TCGGCCCTGA GCAACTCCAT CATGTACTTC AGCCACTTCG
 451 TGCCGGTCTT CCTGCCAGCG AAGCCCACCA CGACGCCAGC GCCGCGACCA
 501 CCAACACCGG CGCCCACCAT CGCGTCGCAG CCCCTGTCCC TGCGCCCAGA
 551 GGCGTGCCGG CCAGCGGCGG GGGCGCGCAGT GCACACGAGG GGGCTGGACT
 601 TCGCCCTGTGA TATCTACATC TGGCCGCCCT TGGCCGGGAC TTGTGGGGTC
 651 CTTCTCCTGT CTTCTCCTGT CACCCTTTAC TGCAACCACA GGAACCGAAG
 701 ACGTGTTTGC AAATGTCCCC GGCCTGTGGT CAAATCGGGA GACAAGCCCA
 751 GCCTTTCGGC GAGATACGTC TAACCCTGTG CAACAGCCAC TACATTACTT
 801 CAAACTGAGA TCCTTCCTTT TGAGGAGCA AGTCCTTCCC TTTCATTTTT
 851 TCCAGTCTTC CTCCCTGTGT ATTCATTCTC ATGATTATTA TTTTAGTGGG
 901 GGCGGGGTGG GAAAGATTAC TTTTTCTTTA TGTGTTTGAC GGGAAACAAA
 951 ACTAGGTAAA ATCTACAGTA CACCACAAGG GTCACAATAC TGTTGTGCGC
1001 ACATCGCGGT AGGGCGTGGA AAGGGGCAGG CCAGAGCTAC CCGCAGAGTT
1051 CTCAGAATCA

1 MALPVTALLL PLALLLHAAR PSQFRVSPLD RTWNLGETVE LKCQVLLSNP
  51 TSGCSWLFQP RGAAASPTFL LYLSQNKPKA AEGLDTQRFS GKRLGDTFVL
 101 TLSDFRRENE GYYFCSALSN SIMYFSHFVP VFLPAKPTTT PAPRPPTPAP
 151 TIASQPLSLR PEACRPAAGG AVHTRGLDFA CDIYIWAPLA GTCGVLLLSL
 201 VITLYCNHRN RRRVCKCPRP VVKSGDKPSL SARYV*
```

FIG. 9

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
        (A) LENGTH: 840 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 22..807

(xi) SEQUENCE DESCRIPTION: SEQ ID NO:1:

```
CCATTTCAAC TTTAACACAG C ATG ATC GAA ACA TAC AAC CAA ACT TCT CCC         51
                       Met Ile Glu Thr Tyr Asn Gln Thr Ser Pro
                         1               5                  10

CGA TCT GCG GCC ACT GGA CTG CCC ATC AGC ATG AAA ATT TTT ATG TAT         99
Arg Ser Ala Ala Thr Gly Leu Pro Ile Ser Met Lys Ile Phe Met Tyr
                15                  20                  25

TTA CTT ACT GTT TTT CTT ATC ACC CAG ATG ATT GGG TCA GCA CTT TTT        147
Leu Leu Thr Val Phe Leu Ile Thr Gln Met Ile Gly Ser Ala Leu Phe
             30                  35                  40

GCT GTG TAT CTT CAT AGA AGG TTG GAC AAG ATA GAA GAT GAA AGG AAT        195
Ala Val Tyr Leu His Arg Arg Leu Asp Lys Ile Glu Asp Glu Arg Asn
         45                  50                  55

CTT CAT GAA GAT TTT GTA TTC ATG AAA ACG ATA CAG AGA TGC AAC ACA        243
Leu His Glu Asp Phe Val Phe Met Lys Thr Ile Gln Arg Cys Asn Thr
     60                  65                  70

GGA GAA AGA TCC TTA TCC TTA CTG AAC TGT GAG GAG ATT AAA AGC CAG        291
Gly Glu Arg Ser Leu Ser Leu Leu Asn Cys Glu Glu Ile Lys Ser Gln
 75                  80                  85                  90

TTT GAA GGC TTT GTG AAG GAT ATA ATG TTA AAC AAA GAG GAG ACG AAG        339
Phe Glu Gly Phe Val Lys Asp Ile Met Leu Asn Lys Glu Glu Thr Lys
                 95                 100                 105

AAA GAA AAC AGC TTT GAA ATG CAA AAA GGT GAT CAG AAT CCT CAA ATT        387
Lys Glu Asn Ser Phe Glu Met Gln Lys Gly Asp Gln Asn Pro Gln Ile
            110                 115                 120

GCG GCA CAT GTC ATA AGT GAG GCC AGC AGT AAA ACA ACA TCT GTG TTA        435
Ala Ala His Val Ile Ser Glu Ala Ser Ser Lys Thr Thr Ser Val Leu
        125                 130                 135

CAG TGG GCT GAA AAA GGA TAC TAC ACC ATG AGC AAC AAC TTG GTA ACC        483
Gln Trp Ala Glu Lys Gly Tyr Tyr Thr Met Ser Asn Asn Leu Val Thr
    140                 145                 150

CTG GAA AAT GGG AAA CAG CTG ACC GTT AAA AGA CAA GGA CTC TAT TAT        531
Leu Glu Asn Gly Lys Gln Leu Thr Val Lys Arg Gln Gly Leu Tyr Tyr
155                 160                 165                 170

ATC TAT GCC CAA GTC ACC TTC TGT TCC AAT CGG GAA GCT TCG AGT CAA        579
Ile Tyr Ala Gln Val Thr Phe Cys Ser Asn Arg Glu Ala Ser Ser Gln
                175                 180                 185

GCT CCA TTT ATA GCC AGC CTC TGC CTA AAG TCC CCC GGT AGA TTC GAG        627
Ala Pro Phe Ile Ala Ser Leu Cys Leu Lys Ser Pro Gly Arg Phe Glu
            190                 195                 200
```

```
AGA ATC TTA CTC AGA GCT GCA AAT ACC CAC AGT TCC GCC AAA CCT TGC       675
Arg Ile Leu Leu Arg Ala Ala Asn Thr His Ser Ser Ala Lys Pro Cys
            205                 210                 215

GGG CAA CAA TCC ATT CAC TTG GGA GGA GTA TTT GAA TTG CAA CCA GGT       723
Gly Gln Gln Ser Ile His Leu Gly Gly Val Phe Glu Leu Gln Pro Gly
        220                 225                 230

GCT TCG GTG TTT GTC AAT GTG ACT GAT CCA AGC CAA GTG AGC CAT GGC       771
Ala Ser Val Phe Val Asn Val Thr Asp Pro Ser Gln Val Ser His Gly
235                 240                 245                 250

ACT GGC TTC ACG TCC TTT GGC TTA CTC AAA CTC TGAACAGTGT CACCTTGCAG     824
Thr Gly Phe Thr Ser Phe Gly Leu Leu Lys Leu
                255                 260

GCTGTGGTGG AGCTGA                                                     840

(2) INFORMATION FOR SEQ ID NO:2:

(i) SEQUENCE CHARACTERISTICS:
        (A) LENGTH: 261 amino acids
        (B) TYPE: amino acid
        (D) TOPOLOGY: linear (ii) MOLECULE TYPE: protein (xi) SEQUENCE DESCRIPTION: SEQ ID NO:2:

Met Ile Glu Thr Tyr Asn Gln Thr Ser Pro Arg Ser Ala Ala Thr Gly
  1               5                  10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
        50                  55                  60

Phe Met Lys Thr Ile Gln Arg Cys Asn Thr Gly Glu Arg Ser Leu Ser
 65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
                100                 105                 110

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
        130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
```

260

(2) INFORMATION FOR SEQ ID NO:3:

(i) SEQUENCE CHARACTERISTICS:
        (A) LENGTH: 151 amino acids
        (B) TYPE: amino acid
        (D) TOPOLOGY: linear (ii) MOLECULE TYPE: protein (xi) SEQUENCE DESCRIPTION: SEQ ID NO:3:

```
Phe Glu Met Gln Lys Gly Asp Gln Asn Pro Gln Ile Ala Ala His Val
  1               5                  10                  15

Ile Ser Glu Ala Ser Ser Lys Thr Thr Ser Val Leu Gln Trp Ala Glu
             20                  25                  30

Lys Gly Tyr Tyr Thr Met Ser Asn Asn Leu Val Thr Leu Glu Asn Gly
         35                  40                  45

Lys Gln Leu Thr Val Lys Arg Gln Gly Leu Tyr Tyr Ile Tyr Ala Gln
     50                  55                  60

Val Thr Phe Cys Ser Asn Arg Glu Ala Ser Gln Ala Pro Phe Ile
 65                  70                  75                  80

Ala Ser Leu Cys Leu Lys Ser Pro Gly Arg Phe Glu Arg Ile Leu Leu
                 85                  90                  95

Arg Ala Ala Asn Thr His Ser Ser Ala Lys Leu Gly Gly Gln Gln Ser
                100                 105                 110

Ile His Leu Gly Gly Val Phe Glu Leu Gln Pro Gly Ala Ser Val Phe
            115                 120                 125

Val Asn Val Thr Asp Pro Ser Gln Val Ser His Gly Thr Gly Phe Thr
        130                 135                 140

Ser Phe Gly Leu Leu Lys Leu
145                 150
```

(2) INFORMATION FOR SEQ ID NO:4:

(i) SEQUENCE CHARACTERISTICS:
        (A) LENGTH: 151 amino acids
        (B) TYPE: amino acid
        (D) TOPOLOGY: linear (ii) MOLECULE TYPE: protein (xi) SEQUENCE DESCRIPTION: SEQ ID NO:4:

```
Phe Glu Met Gln Arg Gly Asp Glu Asp Pro Gln Ile Ala Ala His Val
  1               5                  10                  15

Val Ser Glu Ala Asn Ser Asn Ala Ala Ser Val Leu Gln Trp Ala Lys
             20                  25                  30

Lys Gly Tyr Tyr Thr Met Lys Ser Asn Leu Val Met Leu Glu Asn Gly
         35                  40                  45

Lys Gln Leu Thr Val Lys Arg Glu Gly Leu Tyr Tyr Tyr Thr Gln
     50                  55                  60

Val Thr Phe Cys Ser Asn Arg Glu Pro Ser Ser Gln Arg Pro Phe Ile
 65                  70                  75                  80

Val Gly Leu Trp Leu Lys Pro Ser Ile Gly Ser Glu Arg Ile Leu Leu
                 85                  90                  95

Lys Ala Ala Asn Thr His Ser Ser Ser Gln Leu Cys Glu Gln Gln Ser
                100                 105                 110

Val His Leu Gly Gly Tyr Phe Glu Leu Gln Ala Gly Ala Ser Val Phe
            115                 120                 125
```

```
Val Asn Val Thr Glu Ala Ser Gln Tyr Ile His Arg Val Gly Phe Ser
    130                 135                 140

Ser Phe Gly Leu Leu Lys Leu
145                 150
```

(2) INFORMATION FOR SEQ ID NO:5:

(i) SEQUENCE CHARACTERISTICS:
        (A) LENGTH: 157 amino acids
        (B) TYPE: amino acid
        (D) TOPOLOGY: linear (ii) MOLECULE TYPE: protein (xi) SEQUENCE DESCRIPTION: SEQ ID NO:5:

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
        50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Ile Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

(2) INFORMATION FOR SEQ ID NO:6:

(i) SEQUENCE CHARACTERISTICS:
        (A) LENGTH: 155 amino acids
        (B) TYPE: amino acid
        (D) TOPOLOGY: linear (ii) MOLECULE TYPE: protein (xi) SEQUENCE DESCRIPTION: SEQ ID NO:6:

```
Pro Lys Met His Leu Ala His Ser Thr Leu Lys Pro Ala Ala His Leu
1               5                   10                  15

Ile Asn Asp Pro Ser Lys Gln Asn Ser Leu Leu Trp Arg Ala Asn Thr
                20                  25                  30

Asp Arg Ala Phe Leu Gln Asp Gly Phe Ser Leu Ser Ser Asn Asn Ser
            35                  40                  45

Leu Leu Val Pro Thr Ser Gly Ile Tyr Phe Tyr Ser Gln Val Val
        50                  55                  60

Phe Ser Gly Lys Ala Tyr Ser Pro Lys Ala Thr Ser Ser Pro Ile Tyr
65                  70                  75                  80

Leu Ala His Glu Val Gln Leu Phe Ser Ser Gln Tyr Pro Phe His Val
                85                  90                  95

Pro Leu Leu Ser Ser Gln Lys Met Val Tyr Pro Gly Leu Gln Glu Pro
            100                 105                 110
```

```
Trp Leu His Ser Met Tyr His Gly Ala Ala Phe Gln Leu Thr Gln Gly
        115                 120                 125

Asp Gln Leu Ser Thr His Thr Asp Gly Ile Pro His Leu Val Leu Ser
        130                 135                 140

Pro Ser Thr Val Phe Phe Gly Ala Gly Ala Leu
145                 150                 155

(2) INFORMATION FOR SEQ ID NO:7:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:7:

Leu Asp Phe Ala Cys Asp Pro Asp Pro Arg Arg Leu Asp Lys Ile
1               5                   10                  15

(2) INFORMATION FOR SEQ ID NO:8:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:8:

Leu Asp Phe Ala Cys Asp Pro Asp Pro Arg Tyr Leu Gln Val Ser
1               5                   10                  15

(2) INFORMATION FOR SEQ ID NO:9:

(i) SEQUENCE CHARACTERISTICS:
        (A) LENGTH: 972 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GCTGGCTAAA GGAGCAGTTT CCCCGACCCT ACACGCCTCC CCCACCGCAC CTCCTCCGCC      60

CTGTTCCTGG GCCCCTCCCC TAGAGCCCTA GCTTGACCTA AGCTGCTTGC TGGTGGAGAG     120

CACACCATGG CCTCACCGTT GACCCGCTTT CTGTCGCTGA ACCTGCTGCT GCTGGGTGAG     180

TCGATTATCC TGGGGAGTGG AGAAGCTAAG CCACAGGCAC CCGAACTCCG AATCTTTCCA     240

AAGAAAATGG ACGCCGAACT TGGTCAGAAG GTGGACCTGG TATGTGAAGT GTTGGGGTCC     300

GTTTCGCAAG GATGCTCTTG GCTCTTCCAG AACTCCAGCT CCAAACTCCC CCAGCCCACC     360

TTCGTTGTCT ATATGGCTTC ATCCCACAAC AAGATAACGT GGGACGAGAA GCTGAATTCG     420

TCGAAACTGT TTTCTGCCAT GAGGGACACG AATAATAAGT ACGTTCTCAC CCTGAACAAG     480

TTCAGCAAGG AAAACGAAGG CTACTATTTC TGCTCAGTCA TCAGCAACTC GGTGATGTAC     540

TTCAGTTCTG TCGTGCCAGT CCTTCAGAAA GTGAACTCTA CTACTACCAA GCCAGTGCTG     600

CGAACTCCCT CACCTGTGCA CCCTACCGGG ACATCTCAGC CCAGAGACC AGAAGATTGT      660

CGGCCCCGTG GCTCAGTGAA GGGGACCGGA TTGGACTTCG CCTGTGATAT TTACATCTGG     720

GCACCCTTGG CCGGAATCTG CGTGGCCCTT CTGCTGTCCT TGATCATCAC TCTCATCTGC     780

TACCACAGGA GCCGAAAGCG TGTTTGCAAA TGTCCCAGGC CGCTAGTCAG ACAGGAAGGC     840
```

```
AAGCCCAGAC CTTCAGAGAA AATTGTGTAA AATGGCACCG CCAGGAAGCT ACAACTACTA        900

CATGACTTCA GAGATCTCTT CTTGCAAGAG GCCAGGCCCT CCTTTTTCAA GTTTCCTGCT        960

GTCTTATGTA TT                                                            972
```

(2) INFORMATION FOR SEQ ID NO:10:

(i) SEQUENCE CHARACTERISTICS:
        (A) LENGTH: 249 amino acids
        (B) TYPE: amino acid
        (D) TOPOLOGY: linear (ii) MOLECULE TYPE: peptide (xi) SEQUENCE DESCRIPTION: SEQ ID NO:10:

```
Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala Lys Pro Gln Ala Pro
            20                  25                  30

Glu Leu Arg Ile Phe Pro Lys Lys Met Asp Ala Glu Leu Gly Gln Lys
        35                  40                  45

Val Asp Leu Val Cys Glu Val Leu Gly Ser Val Ser Gln Gly Cys Ser
50                  55                  60

Trp Leu Phe Gln Asn Ser Ser Lys Leu Pro Gln Pro Thr Phe Val
65                  70                  75                  80

Val Tyr Met Ala Ser Ser His Asn Lys Ile Thr Trp Asp Glu Lys Leu
                85                  90                  95

Asn Ser Ser Lys Leu Phe Ser Ala Met Arg Asp Thr Asn Asn Lys Tyr
            100                 105                 110

Val Leu Thr Leu Asn Lys Phe Ser Lys Glu Asn Glu Gly Tyr Tyr Phe
        115                 120                 125

Cys Ser Val Ile Ser Asn Ser Val Met Tyr Phe Ser Ser Val Val Pro
130                 135                 140

Val Leu Gln Lys Val Asn Ser Thr Thr Thr Lys Pro Val Leu Arg Thr
145                 150                 155                 160

Pro Ser Pro Val His Pro Thr Gly Thr Ser Gln Pro Gln Arg Pro Glu
                165                 170                 175

Asp Cys Arg Pro Arg Gly Ser Val Lys Gly Thr Gly Leu Asp Phe Ala
            180                 185                 190

Cys Asp Ile Tyr Ile Trp Ala Pro Leu Ala Gly Ile Cys Val Ala Leu
        195                 200                 205

Leu Leu Ser Leu Ile Ile Thr Leu Ile Cys Tyr His Arg Ser Arg Lys
210                 215                 220

Arg Val Cys Lys Cys Pro Arg Pro Leu Val Arg Gln Glu Gly Lys Pro
225                 230                 235                 240

Arg Pro Ser Glu Lys Ile Val Asn Gly
                245
```

(2) INFORMATION FOR SEQ ID NO:11:

(i) SEQUENCE CHARACTERISTICS:
        (A) LENGTH: 1060 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

-continued

```
CGGCTCCCGC GCCGCCTCCC CTCGCGCCCG AGCTTCGAGC CAAGCAGCGT CCTGGGGAGC     60

GCGTCATGGC CTTACCAGTG ACCGCCTTGC TCCTGCCGCT GGCCTTGCTG CTCCACGCCG    120

CCAGGCCGAG CCAGTTCCGG GTGTCGCCGC TGGATCGGAC CTGGAACCTG GGCGAGACAG    180

TGGAGCTGAA GTGCCAGGTG CTGCTGTCCA ACCCGACGTC GGGCTGCTCG TGGCTCTTCC    240

AGCCGCGCGG CGCCGCCGCC AGTCCCACCT TCCTCCTATA CCTCTCCCAA ACAAGCCCA     300

AGGCGGCCGA GGGGCTGGAC ACCCAGCGGT TCTCGGGCAA GAGGTTGGGG GACACCTTCG    360

TCCTCACCCT GAGCGACTTC CGCCGAGAGA ACGAGGGCTA CTATTTCTGC TCGGCCCTGA    420

GCAACTCCAT CATGTACTTC AGCCACTTCG TGCCGGTCTT CCTGCCAGCG AAGCCCACCA    480

CGACGCCAGC GCCGCGACCA CCAACACCGG CGCCCACCAT CGCGTCGCAG CCCCTGTCCC    540

TGCGCCCAGA GGCGTGCCGG CCAGCGGCGG GGGCGCAGT GCACACGAGG GGGCTGGACT     600

TCGCCTGTGA TATCTACATC TGGGCGCCCT TGGCCGGGAC TTGTGGGGTC CTTCTCCTGT    660

CACTGGTTAT CACCCTTTAC TGCAACCACA GGAACCGAAG ACGTGTTTGC AAATGTCCCC    720

GGCCTGTGGT CAAATCGGGA GACAAGCCCA GCCTTTCGGC GAGATACGTC TAACCCTGTG    780

CAACAGCCAC TACATTACTT CAAACTGAGA TCCTTCCTTT TGAGGGAGCA AGTCCTTCCC    840

TTTCATTTTT TCCAGTCTTC CTCCCTGTGT ATTCATTCTC ATGATTATTA TTTTAGTGGG    900

GGCGGGGTGG GAAAGATTAC TTTTTCTTTA TGTGTTTGAC GGGAAACAAA ACTAGGTAAA    960

ATCTACAGTA CACCACAAGG GTCACAATAC TGTTGTGCGC ACATCGCGGT AGGGCGTGGA   1020

AAGGGGCAGG CCAGAGCTAC CCGCAGAGTT CTCAGAATCA                         1060
```

(2) INFORMATION FOR SEQ ID NO:12:

(i) SEQUENCE CHARACTERISTICS:
        (A) LENGTH: 235 amino acids
        (B) TYPE: amino acid
        (D) TOPOLOGY: linear (ii) MOLECULE TYPE: peptide (xi) SEQUENCE DESCRIPTION: SEQ ID NO:12:

```
Met Ala Leu Pro Val Thr Ala Leu Leu Leu Pro Leu Ala Leu Leu Leu
 1               5                  10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175
```

```
Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GCGAAGCTTT CAGTCAGCAT GATAGAAACA                                    30

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CGCTCTAGAT GTTCAGAGTT TGAGTAAGCC                                    30

(2) INFORMATION FOR SEQ ID NO:15:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CGAAGCTTGG ATCCGAGGAG GTTGGACAAG ATAGAAGAT                          39
```

FUSION PROTEINS COMPRISING GP39 AND CD8

This is a division of application Ser. No. 07/940,605, filed Sep. 4, 1992 now issued as U.S. Pat. No. 5,540,926 on Jul. 30, 1996.

1. INTRODUCTION

The present invention relates to soluble ligands for CD40 and, in particular, to human gp39 protein and soluble ligands derived therefrom which may be used in methods of promoting B-cell proliferation.

2. BACKGROUND OF THE INVENTION 2.1. The B-Cell Antigen, CD40

CD40 is an approximately 50 kDa glycoprotein expressed on the surface of B cells, follicular dendritic cells, normal basal epithelium, and some carcinoma and melanoma derived cell lines (Paulie et al., 1985, Cancer Immunol. Immunother., 20:23–28; Clark and Ledbetter, 1986, Proc. Natl. Acad. Sci. 83:4494–4498; Ledbetter et al., 1987, J. Immunol. 138:788–794; Ledbetter et al., 1987, in "Leukocyte Typing III," McMichael, ed., Oxford U. Press pp. 432–435; Paulie et al., 1989, J. Immunol. 142:590–595; Young et al., 1989, Int. J. Cancer 43:786–794; Galay et al., 1992, J. Immunol. 149:775). Isolation of a human cDNA encoding CD40 showed that this protein is a type I membrane protein which is significantly related to the members of the nerve growth factor receptor family (Stamenkovic et al., 1989, EMBO J. 8:1403–1410).

The role of CD40 in B cell activation is well established. Crosslinking CD40 with anti-CD40 monoclonal antibodies (mAb) induces B cell aggregation via LFA-I (Gordon et al., 1988, J. Immunol. 140:1425–1430; Barrett et al., 1991, J. Immunol. 146:1722–1729), increases serine/threonine (Einfeld et al., 1988, EMBO J. 7:711–717) and tyrosine (Uckun et al., 1991, J. Biol. Chem. 266:17478–17485) phosphorylation of a number of intracellular substrates, and provides a "competency" signal which allows B cells to proliferate and undergo class switching when stimulated with the appropriate second signal. For example, anti-CD40 mAb can synergize with phorbol myristyl acetate (PMA; Gordon et al., 1987, Eur. J. Immunol. 17:1535–1538) or anti-CD20 Mab (Clark and Ledbetter, 1986, Proc. Natl. Acad. Sci. 83:4494–4498) to induce B cell proliferation, with IL-4 to induce B cell proliferation (Gordon et al., 1987, Eur. J. Immunol. 17:1535–1538; Rousset et al., 1991, J. Exp. Med. 173:705–710) and IgE secretion (Jabara et al., 1990, J. Exp. Med. 172:1861–1864; Rousset et al., 1991, J. Exp. Med. 173:705–710; Gascan et al., 1991, J. Immunol. 147:8–13; Zhang et al., 1991, J. Immunol. 146:1836–1842; Shapira et al. 1992, J. Exp. Med. 175:289–292) and with IL-10 and TGF-β to induce IgA secretion by sIgD$^+$ B cells (DeFrance et al., 1992, J. Exp. Med. 175:671–682). Also, there is evidence that CD40 delivered signals are involved in modulating cytokine production by activated B cells (Cairns et al., 1988, Eur. J. Immunol. 18:349–353; Clark and Shu, 1990, J. Immunol. 145:1400–1406).

Crosslinking of anti-CD40 mAb alone is not sufficient to induce B cell proliferation as demonstrated by the observation that anti-CD40 mAb immobilized on plastic in conjunction with IL-4 is unable to induce vigorous B cell proliferation (Banchereau et al., 1991, Science 251:70–72). However, anti-CD40 mAb immobilized on murine L cells transfected with an Fc receptor, CDw32, are able to induce B cell proliferation in the presence of IL-4 (Banchereau et al., 1991, Science 251:70–72), suggesting that a signal provided by the fibroblasts synergizes with the CD40 signal and IL-4 to drive B cell proliferation.

2.2. The T-Cell Antigen, gp39

Soluble forms of the extracellular domain of human CD40 such as CD40-Ig have been used to show that the CD40 ligand, gp39, is a glycoprotein of approximately 39 kDa expressed on the surface of activated CD4$^+$ murine T cells (Armitage et al., 1992, Nature 357:80–82; Noelle et al., 1992, Proc. Natl. Acad. Sci. USA 89:6550–6554). Interaction with gp39 induces resting B cells to enter the cell cycle and become responsive to the growth and differentiation effects of lymphokines (Armitage et al., 1992, Nature 357:80–82; Noelle et al., 1992, Proc. Natl. Acad. Sci. USA 89:6550–6554).

Recently, a cDNA encoding murine gp39 has been isolated and shown to be functionally active when expressed as a membrane protein on transfected cells (Armitage et al., 1992, Nature 357:80–82). This cDNA encodes a 260 amino acid polypeptide with the typical features of a type II membrane protein and CV1/EBNA cells expressing murine gp39 were shown to induce murine and human B cell proliferation without additional co-stimulus.

3. SUMMARY OF THE INVENTION

The present invention relates to soluble ligands for CD40, and, in particular, to human gp39 protein and soluble ligands derived therefrom. It is based, at least in part, on the discovery, cloning, and expression of the human T cell antigen gp39, a ligand for the CD40 receptor. It is also based, in part, on the preparation of a soluble form of human gp39 which, together with a co-stimulating agent, is able to promote B cell proliferation and differentiation.

The present invention provides for essentially purified and isolated human gp39 protein having a sequence substantially as set forth in FIG. 1, as well as for essentially purified and isolated nucleic acid having a sequence substantially as set forth in FIG. 1 and/or encoding said human gp39 protein.

The present invention further provides for soluble forms of human as well as non-human gp39. In a preferred, non-limiting embodiment of the invention, soluble gp39 may be produced using the expression vector CD8-gp39.

The soluble gp39 of the invention may be used, together with co-stimulating agents, to promote the proliferation of B-cells in vivo or in vitro. Such proliferation may be desirable in the treatment of conditions that would benefit from an augmented immune response, such as acquired immunodeficiency syndrome or for the generation of a cell culture system for long-term B-cell growth.

4. DESCRIPTION OF THE FIGURES

FIG. 1. Nucleotide and predicted amino acid sequence of human gp39 and homology to murine gp39, TNFα and TNFβ. (A) The nucleotide sequence and translated open reading frame are numbered at left. Sites of potential N-linked glycosylation are marked (CHO), the predicted transmembrane domain (TM) is underlined and the two Arg residues located at the junction of the predicted transmembrane and extracellular domains are double underlined. Nucleotide and amino acid numbering is given to the left. (B) Alignment of the predicted amino acid sequence of human gp39 (H-gp39), murine gp39 (M-gp39), human TNFα (H-TNFα), and human TNFβ (H-TNFβ). Amino acids shared by at least three proteins are shown boxed;

similar amino acids shared by at least three of the proteins are shown shaded.

FIG. 2. Soluble recombinant human gp39 and CD72, sgp39 and sCD72. (A) The cDNA fragment encoding the extracellular domain of murine CD8 is designated mu-CD8 EC. The murine CD8 amino terminal secretory signal sequence is shown stippled. The cDNA fragment encoding the extracellular domain of human gp39 or CD72 are designated hu-gp39 EC and hu-CD72 EC, respectively. The amino acid sequences predicted at the site of fusion of the extracellular domain of murine CD8 and human gp39 (italic) or CD72 (italic) are shown below the individual diagrams. Residues introduced at the junction of the two cDNA fragments are shown underlined. The unique Bam HI restriction enzyme recognition site at the junction of the two genes is shown. (B) Radiolabelled proteins from the supernatants of metabolically labeled mock (lanes 1 and 2) of CD8-gp39 (lanes 3 and 4) transfected COS cells were immunoprecipitated based on their interaction with the anti-murine CD8 mAb 53-6 (lanes 1 and 3) or the CD40-Ig (lanes 2 and 4) and analyzed by SDS-PAGE under reducing conditions as described in the text. The electrophoretic mobility of molecular mass standards of the indicated mass in kDa are shown to the left. (C) Radiolabelled proteins from the supernatants of metabolically labeled mock (lanes 1–4) and CD8–CD72 (lanes 5–8) transfected COS cells were recovered based on their reactivity with the anti-murine mAb 53.6 (lanes 1 and 5), the anti-CD72 mAb J3I01 (lanes 2 and 6), the anti-CD72 mAb BU41 (lanes 3 and 7) and CD40-Ig (lanes 4 and 8) and analyzed by SDS-PAGE under reducing conditions as described in the text. The electrophoretic mobility of molecular mass standards of the indicated mass in kDa are shown to the left.

FIG. 3. Binding of sgp39 or CD40-Ig to transfected COS cells. COS cells transfected with either a gp39 (A and B) or a CD40 (C–F) cDNA expression plasmid were examined for their ability to bind either soluble recombinant CD40 (A and B), or soluble recombinant gp39 (C and D), or the anti-CD40 mAb G28-5 (E and F) as described in the text. Phase (A, C and E) and fluorescent (B, D and F) images of representative fields are shown.

Figure 4:
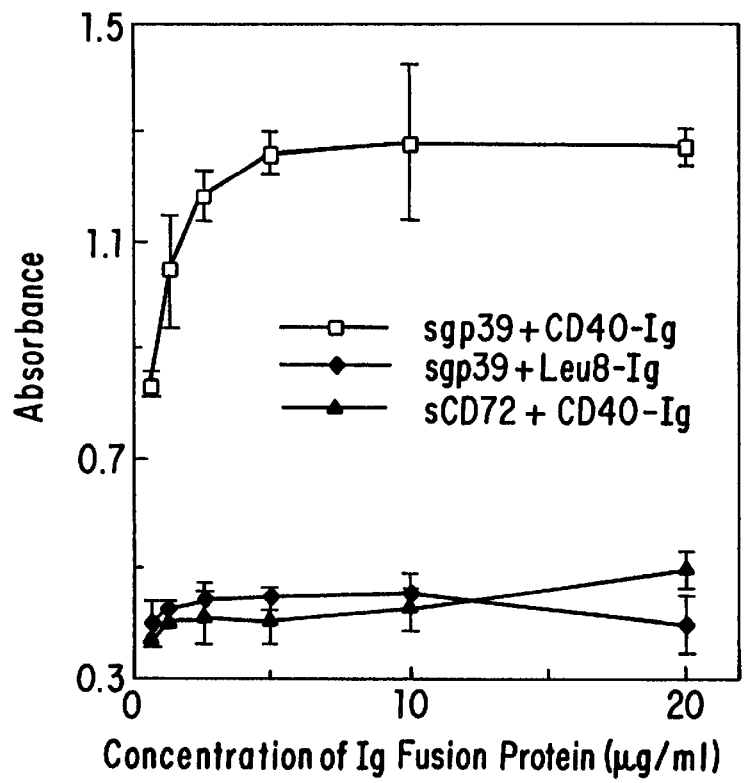

FIG. 4. Characterization of the sgp39/CD40-Ig interaction. The ability of increasing concentrations of CD40-Ig (0.6 µg/ml to 20 µg/ml) and the control immunoglobulin fusion protein, Leu8-Ig (0.6 µg/ml to 20 µg/ml), to bind to immobilized sgp39 was examined by ELISA as described in the text. Likewise the ability of increasing concentrations of CD40-Ig to bind to the immobilized control fusion protein sCD72 was also examined in the same way. In both cases the sgp39 and sCD72 were immobilized on plastic which had been previously coated with the anti-murine CD8 mAb 53-6 as described in the text.

Figure 5:
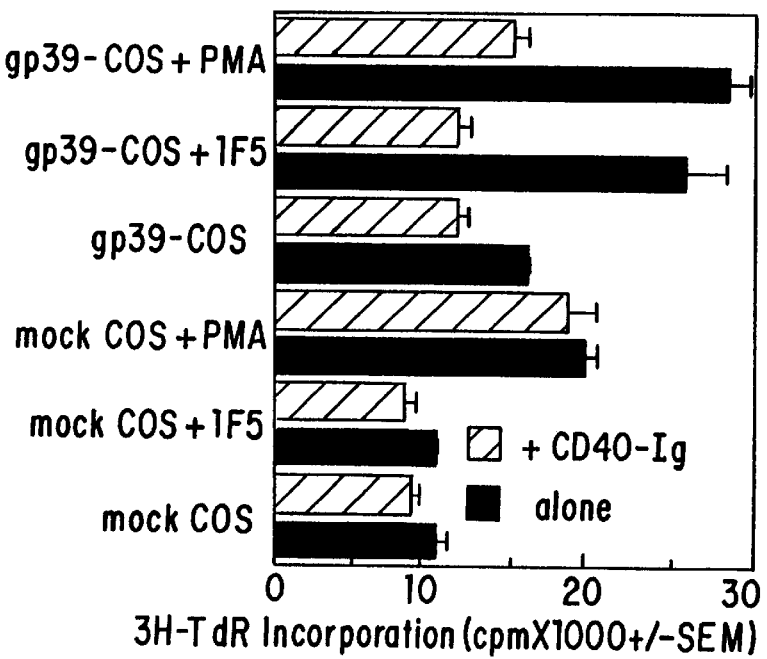

FIG. 5. Activation of human B cells by surface bound gp39. The ability of gp39-expressing COS cells (gp39-COS) or mock transfected COS cells (mock COS) to stimulate the proliferation of resting human peripheral blood B cells alone or in the presence of the anti-CD20 mAb IF5 (+IF5) or PMA (+PMA) in the absence (solid bars, alone) or presence (hatched bars, +CD40-Ig) of CD40-Ig was examined as described in the text and evaluated by [$^3$H]-thymidine incorporation.

Figure 6:
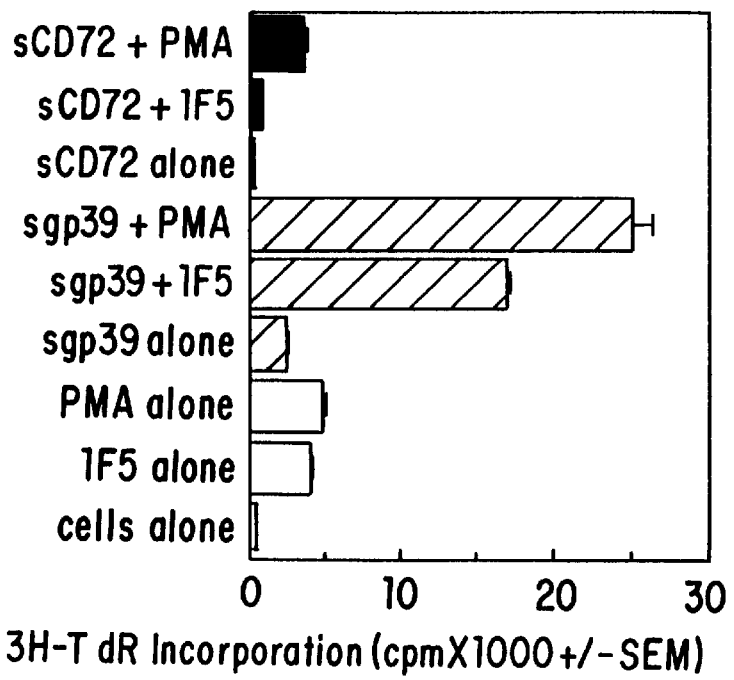

FIG. 6. Activation of human peripheral blood B cell by sgp39. The ability of soluble recombinant gp39 (sgp39, hatched bars) or control soluble recombinant fusion protein (sCD72, solid bars) to stimulate the proliferation of resting human peripheral blood B cells alone or in conjunction with the anti-CD20 mAb IF5 (+IF5) or PMA (+PMA) was examined as described in the text, evaluated by [$^3$H]-thymidine incorporation and compared to that of B cells incubated for an equivalent amount of time in the absence of exogenous stimuli (cells alone, open bars) or in the presence of either IF5 alone or PMA alone (open bars).

FIG. 7. Activation of dense human tonsillar B cells by sgp39. The ability of soluble recombinant gp39 (sgp39, hatched and solid bars) to stimulate the proliferation of dense tonsillar B cells alone or in conjunction with the anti-CD20 mAb IF5 (+IF5) or PMA (+PMA) was examined as described in the text, evaluated by [$^3$H]-thymidine incorporation and compared to that of B cells incubated alone (cells alone, open bars) or in the presence of either IF5 alone or PMA alone (open bars). The ability of CD40-Ig (solid bars) to block the sgp39 driven B cell activation was examined at a concentration of 20 mg/ml (A) and compared to an equal concentration of an irrelevant immunoglobulin fusion protein, Leu-8-Ig (solid bars, B).

FIG. 8. Amino acid and nucleic acid sequence of murine CD8.

FIG. 9. Amino acid and nucleic acid sequence of human CD8.

5. DETAILED DESCRIPTION OF THE INVENTION

For clarity of description and not by way of limitation, the detailed description of the invention is divided into the following subsections:

(i) cloning and expression of human gp39 (hgp39);

(ii) preparation of soluble gp39 (sgp39); and (iii) utility of the invention.

5.1. Cloning and Expression of Human gp39

The present invention provides for essentially purified and isolated nucleic acids encoding hgp39, for essentially purified and isolated hgp39 protein, and for methods of expressing hgp39. The complete nucleic acid sequence of hgp39 (corresponding to cDNA) and the complete amino acid sequence of hgp39 are presented in FIG. 1 and contained in plasmid CDM8-hgp39, deposited with the American Type Culture Collection (ATCC) as *Escherichia coli*, CDM8 MC1061/p3-hgp39 and assigned accession No. 69050. An example of an expression vector that may be used to produce soluble hgp39 (shgp39) is plasmid CDM7B⁻-shgp39 which has been deposited with the ATCC as *Escherichia coli* CDM7B⁻ MC1061/p3-shgp39 and assigned accession number 69049.

In particular embodiments, the present invention provides for an essentially purified and isolated nucleic acid having a sequence substantially as set forth in FIG. 1, and for an essentially purified and isolated nucleic acid encoding a protein having a sequence substantially as set forth in FIG. 1. The present invention further provides for an essentially purified and isolated protein having a sequence substantially as set forth in FIG. 1.

The term "substantially", as used herein, indicates that the sequences set forth in FIG. 1 may be altered by mutations such as substitutions, additions, or deletions that result in a molecule functionally equivalent to a protein having a sequence as set forth in FIG. 1. For example, due to the degeneracy of the genetic code, the nucleic acid sequence as set forth in FIG. 1 may be altered provided that the final sequence encodes a protein having the same sequence as depicted in FIG. 1 or a functionally equivalent sequence;

i.e., an amino acid sequence in which functionally equivalent amino acids, such as amino acids of the same group (e.g. hydrophobic, polar, basic, or acidic) are substituted into the protein.

For example, one or more amino acid residues within the sequence can be substituted by another amino acid of a similar polarity which acts as a functional equivalent, resulting in a silent alteration. Substitutes for amino acid within the sequence may be selected from other members of the class to which the amino acid belongs. For example, the nonpolar (hydrophobic) amino acids include alanine, leucine, isoleucine, valine, proline, phenylalanine, tryptophan and glutamine. The positively charged (basic) amino acids include arginine, lysine, and histidine. The negatively charged (acidic) amino acids include aspartic acid and glutamic acid. The proteins of the invention may also be differentially modified during or after translation, e.g. by phosphorylation, glycosylation, crosslinking, acylation, proteolytic cleavage, etc.

Genomic or cDNA clones containing hgp39-encoding sequences may be identified, for example, by synthesizing oligonucleotide probes that contain a portion of the hgp39 sequence depicted in FIG. 1, and using such probes in hybridization reaction by the method of Benton and Davis (1977, Science 196:180) or Grunstein and Hogness (1975, Proc. Natl. Acad. Sci. U.S.A. 72:3961–3965). Similarly, oligonucleotide primers containing a portion of the hgp39 sequence depicted in FIG. 1 may be prepared and used in polymerase chain reactions (Saiki et al., 1985, Science 230:1350–1354), using, for example, cDNA from activated T lymphocytes as template, to generate fragments of hgp39 sequence that may be pieced together to form or otherwise identify a full-length sequence encoding hgp39.

In a specific, non-limiting embodiment of the invention, cDNA encoding hgp39 may be isolated and characterized as follows. CD40-Ig, as described in Noelle et al., 1992, Proc. Natl. Acad. Sci. U.S.A. 89:6550–6554, may be modified by the introduction of three mutations, namely L234F, L235E, and G237A, in the immunoglobulin domain, which reduce the binding to Fc receptors. The modified CD40-Ig may be purified from COS cell supernatants as described in Aruffo, 1990, Cell 61:1303–1313. Human gp39 cDNA may be amplified by polymerase chain reaction (PCR) from a library prepared from phytohemagglutin-activated human peripheral blood T-cells (Camerini et al., 1989, Nature 342:78–82). The oligonucleotide primers may be designed based on the sequence of murine gp39 (Armitage et al., 1992, Nature 357:80–82) and may be engineered to include cleavage sites for the restriction enzymes XbaI and HindIII, to be used in subcloning the PCR product. For example, and not by way of limitation, the following oligonucleotides may be used: 5'-GCG AAG CTT TCA GTC AGC ATG ATA GAA ACA-3'SEQUENCE ID NO. 15 and 5-CGC TCT AGA TGT TCA GAG TTT GAG TAA GCC-3'SEQUENCE ID NO. 14. Amplification may be performed with Taq polymerase and the reaction buffer recommended by the manufacturer (Perkin Elmer Cetus Corp., Norwalk, Conn.) using 30 cycles of the following temperature program: 2 min., 95° C.; 2 min., 55° C.; 3 min., 72° C. The PCR product may be digested with HindIII and XbaI and should be found to contain an internal HindIII restriction site. The resulting HindIII-XbaI fragment may then be subcloned into a suitable vector, such as, for example, the CDM8 vector. The complete gene product may be constructed by subcloning the HindIII-HindIII fragment into the vector containing the HindIII-XbaI fragment. The resulting construct may then be transfected into COS cells using DEAE-dextran as described in Aruffo et al., 1990, Cell 61:1303–1313. Transfectants may be stained with CD40-Ig (25 µg/ml in DMEM media) followed by FITC-conjugated goat anti-human IgG Fc antibody (1:50 dilution in DMEM, TAGO, Burlingame, Calif.) and visualized by immunofluorescence microscopy. A clone containing the complete hgp39 sequence may be obtained by colony hybridization as described in Sambrook et al., 1989, in "Molecular Cloning: A Laboratory Manual," Cold Spring Harbor Press, Cold Spring Harbor, NY. The subcloned HindIII-HindIII fragment of the PCR product may be used to generate a $^{32}$P-labelled probe by random primed polymerization. Plasmid DNA from several individual clones may be transfected into COS cells and the transfectants may be stained with CD40-Ig. Clones that give rise to positive-staining COS cell transfectants may then be further characterized by restriction fragment mapping and sequencing.

Once obtained, the hgp39 gene may be cloned or subcloned using any method known in the art. A large number of vector-host systems known in the art may be used. Possible vectors include, but are not limited to, cosmids, plasmids, or modified viruses, but the vector system must be compatible with the host cell used. Such vectors include, but are not limited to, bacteriophages such as lambda derivatives, or plasmids such as pBR322, puC, or Bluescript™ (Stratagene) plasmid derivatives. Recombinant molecules can be introduced into host cells via transformation, transfection, infection, electroporation, etc.

The hgp39 gene may be inserted into a cloning vector which can be used to transform, transfect, or infect appropriate host cells so that many copies of the gene sequence are generated. This can be accomplished by ligating the DNA fragment into a cloning vector which has complementary cohesive termini. However, if the complementary restriction sites used to fragment the DNA are not present in the cloning vector, the ends of the DNA molecules may be enzymatically modified.

In order to express recombinant hgp39, the nucleotide sequence coding for hgp39 protein, or a portion thereof, may be inserted into an appropriate expression vector, i.e, a vector which contains the necessary elements for the transcription and translation of the inserted peptide/protein encoding sequence. The necessary transcription and translation signals can also be supplied by the native hgp39 gene and/or its flanking regions. A variety of host-vector systems may be utilized to express the protein-coding sequence. These include, but are not limited to, mammalian cell systems infected with virus (e.g. vaccinia virus, adenovirus, etc.) or transfected with plasmid expression vector; insect cell systems infected with virus (e.g. baculovirus); microorganisms such as yeast containing yeast vectors, or bacteria transformed with bacteriophage DNA, plasmid DNA, or cosmid DNA. The expression elements of these vectors vary in their strengths and specificities.

Expression of nucleic acid sequence encoding hgp39 protein or a portion thereof may be regulated by a second nucleic acid sequence so that hgp39 protein or peptide is expressed in a host transformed with the recombinant DNA molecule. For example, expression of hgp39 may be controlled by any promoter/enhancer element known in the art. Promoters which may be used to control hgp39 expression include, but are not limited to, the SV40 early promoter region (Benoist and Chambon, 1981, Nature 290:304–310), the cytomegalovirus promoter, the promoter contained in the 3' long terminal repeat of Rous sarcoma virus (Yamamoto et al., 1980, Cell 22:787–797); the herpes thymidine kinase promoter (Wagner et al., 1981, Proc. Natl. Acad. Sci. U.S.A. 78:1441–1445), the regulatory sequences of the metallothionine gene (Brinster et al., 1982, Nature 296:39–42); prokaryotic expression vectors such as the β-lactamase promoter (Villa-Kamaroff et al., 1978, Proc. Natl. Acad. Sci. U.S.A. 75:3727–3731); promoter elements from yeast or other fungi such as the Gal 4 promoter or the alcohol dehydrogenase promoter; and animal transcriptional control regions, such as the immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), the beta-globin gene control region which is active in myeloid cells (Magram et al., 1985, Nature 315:338–340; Kollias et al., 1986, Cell 46:89–94), and other tissue-specific or constitutive promoter/enhancer elements.

Recombinant hgp39 protein or peptide expressed in such systems may be collected and purified by standard methods including chromatography (e.g. ion exchange; affinity (for example, using CD40 as ligand); and sizing column chromatography) centrifugation, differential solubility, or by any other standard technique for the purification of proteins.

According to the present invention, hgp39 protein or peptide may also be synthesized chemically using standard protein synthesis techniques.

5.2. Preparation of Soluble gp39

The present invention also provides for soluble forms of gp39, including both human and non-human gp39. Such soluble forms of gp39 are produced by genetic engineering of gp39-encoding nucleic acid, such as hgp39-encoding nucleic acid (see Section 5.1, supra, and FIG. 1), or Murine gp39-encoding nucleic acid (Armitage et al., 1992, Nature 357:80–82), to produce gp39 fusion proteins which comprise the extracellular domain of gp39, which extends from about amino acid residue 48 to amino acid residue 261. In addition to gp39 amino acid sequence, the fusion proteins of the invention may further comprise a molecular "tag", which may be a portion of a larger protein and which replaces the transmembrane and cytoplasmic domains of gp39 and provides a "handle" that reacts with reagents. Soluble gp39 may also be prepared without a "tag" by replacing the cytoplasmic and transmembrane domain of gp39 with an amino terminal signal peptide derived from a type I membrane protein or a secreted protein.

Because gp39 is a type II membrane protein and is therefore oriented with a carboxy-terminal extracellular domain, the tag is desirably oriented amino-terminal to the gp39 extracellular domain (gp39 ECD). Preferably, the tag peptide contains an amino-terminal secretory signal sequence to allow export of the fusion protein.

Appropriate tag proteins include extracellular protein domains with well defined tertiary structures, so as to minimize the possibility of affecting the tertiary structure of gp39 ECD while increasing the likelihood of successful expression and transport. For example, an ECD protein which is known to have been incorporated into a fusion protein that was synthesized and exported in high yield from an expression system would be likely to be a suitable tag protein for soluble gp39.

Another criterion for selecting a tag protein is the availability of reagents that react with the tag protein. For example, a tag protein to which one or more monoclonal antibodies have been produced offers the advantage of providing a "handle" which may be detected or manipulated by monoclonal antibody.

Suitable tag proteins include but are not limited to extracellular domains of type I membrane proteins such as CD8, secreted proteins such as IL-4, Fc domains of immunoglobulins, etc. In preferred, specific, nonlimiting embodiments of the invention, the tag protein is the murine CD8 that comprises its extracellular domain (ECD) (described by Nakauchi et al., 1985, Proc. Natl. Acad. Sci. U.S.A. 82:5126–5130) or its human equivalent (Kavathas et al., 1984, Proc. Natl. Acad. Sci. U.S.A. 81:7688). The nucleotide and amino acid sequences of murine CD8 are presented in FIG. 8; the ECD is found between amino acid residues 1 and 174 (numbering from the first ATG of nucleic acid sequence), as encoded by that portion of the nucleic acid between nucleotide residues 121 and 708. The nucleotide and amino acid sequences of corresponding human CD8 are presented in FIG. 9; the ECD is found between amino acid residues 1 and 161 as encoded by that portion of the nucleic acid between nucleotide residues 129 and 611.

Figure 2A:
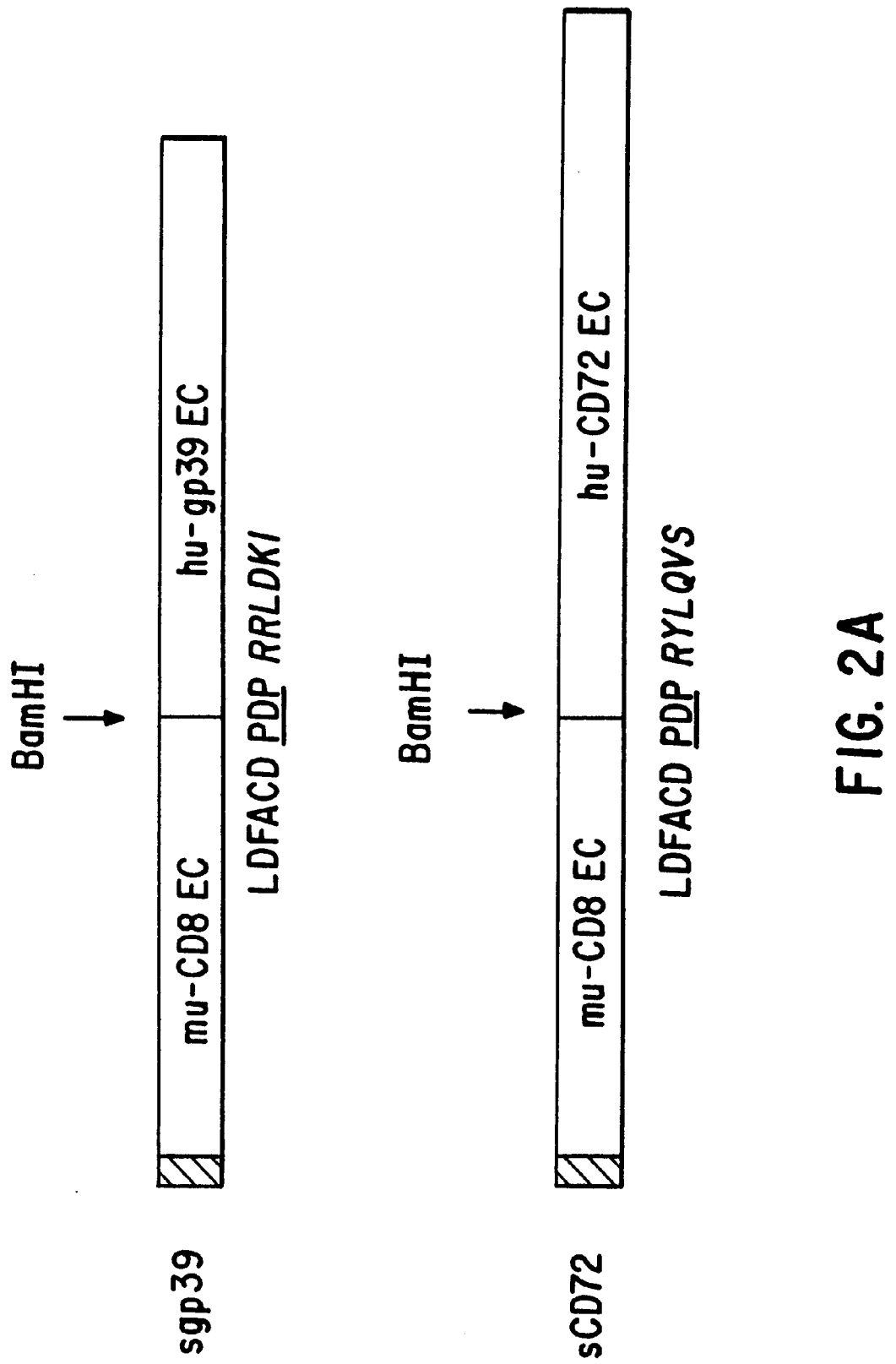

For example, and not by way of limitation, the construct depicted in FIG. 2A and described infra in Section 7 may be used to produce soluble gp39 (sgp39). This construct may be prepared as follows:

The ECD of hgp39 may be amplified from a cDNA library prepared from mRNA from phytohemagglutinin (PHA)-activated human peripheral blood lymphocytes. The oligonucleotide primers may be designed based on the sequence set forth in FIG. 1 and may be engineered so as to place a restriction enzyme cleavage site (e.g. a BamHI cleavage site) is at the 5' end of the gene such that the reading frame may be preserved when the chimeric gene is constructed. For example, oligonucleotides which may be used are 5'-CGA AGC TTG GAT CCG AGG AGG TTG GAC AAG ATA GAA GAT-3' SEQUENCE ID NO. 15 and 5'-CGC TCT AGA TGT TCA GAG TTT GAG TAA GCC-3' SEQUENCE ID NO. 14. Polymerase chain reaction may be performed using Pfu polymerase with buffer supplied by the manufacturer (Stratagene, LaJolla, Calif.) with the following temperature program: 5 min., 95° C.; 2 min., 72° C., 2 min., 55° C.; 40 cycles of amplification consisting of 1 min., 95° C.; 2 min., 55° C.; 3 min., 72° C.; 10 min., 72° C. The PCR product may be digested with BamHI and XbaI and subcloned into a vector containing the gene encoding either the murine CD8 (Lyt2a) ECD or its human equivalent. The resulting construct may then be transfected into COS cells and then expressed to form sgp39, which may then be purified by absorption and elution from an affinity column which contains either CD40-Ig or an anti-murine CD8 mAb, such as 53-6, immobilized on a solid support such as sepharose beads.

It may be desirable to confirm that sgp39 fusion proteins prepared from the gp39 ECD and various tags are capable of binding to CD40. For example, and not by way of limitation, the binding of sgp39 to CD40 may be confirmed in an ELISA assay in which wells of a 96-well plate may be coated with anti-tag antibody, washed with phosphate buffered saline (PBS) containing 0.05 percent Tween-20 (TPBS) and then blocked with 1X specimen Diluent Concentrate (Genetic Systems, 225 μl/well, 2 hours, room temperature). Wells may then be washed with TPBS. Supernatants from COS cells expressing sgp39 or a negative control may be added (150 μl/well) and plates may be incubated at 4° C. overnight. Wells may then be washed with TPBS and then CD40 (e.g. in the form of CD40-Ig fusion protein) or negative control protein, which may desirably be added as serial dilutions in PBS containing 1 mM $CaCl_2$ and 1 mM $MgCl_2$, 20 μg/ml to 0.6 μg/ml, 100 μl/well, 1 hr., room temp.). Wells may then be washed with TPBS and binding of CD40 to the sgp39-coated wells detected; for example, binding of CD40-Ig to sgp39-coated wells may be detected by adding peroxidase-conjugated goat F(ab')$_2$ anti-human IgG followed by chromogenic substrate (e.g. Genetic Systems chromogen diluted 1:100 in EIA Buffered Substrate, Genetic Systems, 100 μl/well). The chromogenic reaction may be stopped after 10 minutes with the addition of Stop Buffer (Genetic Systems, 100 μl/well) and the absorbance may be measured on an ELISA reader at dual wavelengths (450 nm, 630 nm). Alternatively, ELISA may be performed by immobilization of CD40 (e.g. CD40-Ig) on plates coated with antibody (e.g. goat anti-human Fc), and binding of sgp39 from increasing dilutions of COS cell supernatant may be detected using anti-tag antibody.

Additionally, the ability of sgp39.to bind to CD40 may be ascertained by B cell proliferation assay as follows. Peripheral blood mononuclear cells may be isolated by centrifugation through Lymphocyte Separation Medium (Litton Bionetics, Kensington, Md.). Human B Lymphocytes may be enriched from PBMC by passage of cells over nylon columns (Wako Chemicals USA, Inc., Richmond, Va.) and harvesting of adherent cells. The cells may then be treated with leu—leu methyl ester (Sigma, St. Louis, Mo.) to deplete monocytes and NK cells. The resulting cell population may be analyzed by flow cytometry on an EPICS C (Coulter Electronics, Hialeah, Fla.) to determine the percentage of B cells.

Tonsillar B cells may be prepared from intact tonsils by mincing to produce a tonsillar cell suspension. The cells may then be centrifuged through Lymphocyte Separation Medium, washed twice, and then fractionated on a discontinuous Percoll gradient. Cells with a density greater than 50 percent may be collected, washed twice, and used in proliferation assays.

Measurement of proliferation may be performed by culturing B cells in quadruplicate samples in flat-bottomed 96-well microtiter plates at 5 x 10$^4$ cells per well in complete RPMI medium containing 10 percent fetal calf serum. Supernatants of COS cells expressing sgp39 or control construct, diluted 1:4, plus PMA (long/ml, LC Services, Woburn, Mass.) or 1F5 (anti-CD20, 1 μl/ml), may be added to the cultures, and then B-cell proliferation may be measured by uptake of [$^3$H]-thymidine (6.7 Ci/mmol; New England Nuclear, Boston, Mass.) after 5 days of culture and an overnight pulse (cells may be harvested onto glass fiber filters and radioactivity may be measured in a liquid scintillation counter). A boost in B-cell proliferation above control levels (preferably by at least about 100 percent) associated with a particular form of sgp39 indicates the sgp39 interacts with CD40 on the surface of B cells and is biologically active.

The present invention provides for an essentially purified and isolated nucleic acid comprising a sequence substantially as set forth in FIG. 1 from nucleotide residues 160 to 787, which may be used toward the production of the fusion proteins of the invention. Accordingly, the present invention also provides for an essentially purified and isolated nucleic acid comprising a sequence substantially as set forth in FIG. 1 from nucleotide residues 160 to 787 and further comprising a sequence encoding an extracellular domain of a protein other than a gp39 protein (that is, human or non-human gp39 protein); in preferred embodiments, this other protein is murine or human CD8 protein. In a specific, nonlimiting embodiment of the invention, the extracellular domain of this other protein is the extracellular domain of murine or human CD8 from amino acid residues 1 to 174 and 1 to 161, respectively as encoded by the sequence between nucleotides 121–708 as depicted in FIG. 8 and residues 129–611 in FIG. 9. In a preferred, specific, nonlimiting embodiment of the invention, this essentially purified and isolated nucleic acid is contained in plasmid CDM7B$^-$ MC1061/p3-shgp39 as deposited with the ATCC and assigned accession number 69049. The present invention further provides for proteins encoded by such nucleic acids.

For example, the present invention provides for an essentially purified and isolated protein comprising a sequence substantially as set forth in FIG. 1 from amino acid residues 47–261, and for this essentially purified and isolated protein further comprising an extracellular domain of a protein other than a gp39 protein. In preferred embodiments, this other protein is murine or human CD8 protein, and in a specific, nonlimiting embodiment of the invention, the extracellular domain of this other protein is the extracellular domain of murine or human CD8 from amino acid residues 1–174 and 1–161, respectively. In a preferred, specific, nonlimiting embodiment of the invention, the essentially purified and isolated protein is as produced by expression of plasmid CDM7B$^-$ MC1061/p3-shgp39, as deposited with the ATCC and assigned accession number 69049.

5.3. Utility of the Invention

The present invention provides for a method of promoting the proliferation and/or differentiation of CD40-bearing cells comprising exposing the cells to an effective concentration of a soluble gp39 protein, such as the soluble gp39 proteins, both human and non-human, described in Section 5.2, supra.

In preferred embodiments, the invention is used to promote the proliferation and/or differentiation of B-cells which may have been activated prior to exposure to the soluble gp39 protein, concurrently with exposure to soluble gp39 protein or, less preferably, after exposure to soluble gp39 protein, wherein the soluble gp39 protein is still present. Activation of B-cells may be accomplished by any method known in the art, including exposure to co-stimulating agents including, but not limited to, anti-immunoglobulin antibody, antibody directed toward a B-cell surface antigen (e.g. CD20), phorbol myristyl acetate (PMA), ionomycin, or soluble or surface-bound cytokines (e.g IL-4).

An effective concentration of soluble gp39 is defined herein as a concentration which results in an increase in activated B-cell proliferation of at least one hundred percent relative to the proliferation of activated B-cells that are not exposed to gp39 or other mediators of B-cell proliferation (see, for example, Section 5.1 supra and Section 7.1.3 infra). For example, and not by way of limitation, a concentration of between about 0.005–2.5 μg/ml, and most preferably about 0.1–0.25 μg/ml may be used.

As set forth in U.S. Ser. No. 708,075, which is incorporated by reference in its entirety herein, the soluble gp39 proteins of the invention have a number of uses, including in vitro and in vivo uses.

According to one embodiment of the invention, soluble gp39 may be used to produce an in vitro cell culture system for long-term B-cell growth. This may be particularly useful in the preparation of antigen-specific B-cell lines.

In another in vitro embodiment, soluble gp39 may be used to identify or separate cells which express CD40 antigen and/or to assay body fluids for the presence of the CD40 antigen which may or may not be shed. For example, the binding of soluble gp39 to CD40 antigen may be detected by directly or indirectly labeling the soluble gp39, for example, by incorporating radiolabel or chromogen into the soluble gp39 protein (direct labeling) or via anti-gp39 antibody (indirect labeling). In this manner, soluble gp39 may be used diagnostically in vitro to identify CD40 antigen as expressed in tumors, malignant cells, body fluids, etc.

In related embodiments, directly or indirectly labeled soluble gp39 may be used in vivo to image cells or tumors which express the CD40 antigen.

In various other in vivo embodiments, soluble gp39 may be used to increase an immune response, for example, by acting, effectively, as a type of "adjuvant" to increase an immune response to a vaccine. Alternatively, soluble gp39 may be used to increase the immune response of an immunosuppressed individual, such as a person suffering from acquired immunodeficiency syndrome, from malignancy, or an infant or elderly person.

In still further embodiments of the invention, soluble gp39 may be chemically modified so that cells that it binds to are killed. Since all B-cells express CD40, this approach would result in suppression of the immune response. For example, a cytotoxic drug linked to soluble gp39 may be used in vivo to cause immunosuppression in order to cross histocompatibility barriers in transplant patients; alternatively, these modified ligands may be used to control autoimmune diseases.

In further embodiments, soluble gp39 may be used to promote the proliferation and/or differentiation of CD40-bearing cells that are not B cells, for example, sarcoma cells, as a means of directly treating malignancy or as an adjunct to chemotherapy.

The present invention further provides for the production of anti-hgp39 antibodies, polyclonal or monoclonal, using standard laboratory techniques.

The present invention also provides for pharmaceutical compositions that comprise a therapeutically effective concentration of a soluble gp39 as described in Section 5.2, supra, in a suitable pharmacological carrier.

Such pharmaceutical compositions may be administered to a subject in need of such treatment by any suitable mode of administration, including but not limited to intravenous, local injection, subcutaneous, intramuscular, oral, intranasal, rectal, vaginal, intrathecal, etc.

6. EXAMPLE

The Human T Cell Antigen gp39, a Member of the Tumor Necrosis Gene Family, is a Ligand for the CD40 Receptor on B Cells

6.1. Materials and Methods

CD40-Ig, as described in Noelle et al., 1992, Proc. Natl. Acad. Sci. U.S.A. 89:6550–6554, was modified by the introduction of three mutations, namely L234F, L235E, and G237A, in the immunoglobulin domain to reduce the binding to Fc receptors. The modified CD40-Ig was purified from COS cell supernatants as previously described (Aruffo et al., 1990, Cell 61:1303–1313). Human gp39 cDNA was amplified by polymerase chain reaction (PCR) from a library prepared from mRNA isolated from PHA-activated human peripheral blood T-cells (Camerini et al., 1989, Nature 342:78–82). The oligonucleotide primers were designed based on the sequence of the murine gp39 (Armitage et al., 1992, Nature, 357:80–82) and included sites for the restriction enzymes Xba I and HindIII to be used in subcloning the PCR product. The oligonucleotides used were: 5'-GCG AAG CTT TCA GTC AGC ATG ATA GAA ACA-3' SEQUENCE ID NO. 13 and 5'-CGC TCT AGA TGT TCA GAG TTT GAG TAA GCC-3' SEQUENCE ID NO. 14. Amplification was performed with Taq polymerase and the reaction buffer recommended by the manufacturer (Perkin Elmer Cetus Corp., Norwalk, Conn.) using 30 cycles of the following temperature program: 2 min., 95° C.; 2 min., 55° C.; 3 min., 72° C. The PCR product was digested with HindIII and XbaI and was found to contain an internal HindIII restriction site. The HindIII-XbaI fragment was subcloned into the CDM8 vector. The complete gene product was constructed by subcloning the HindIII-HindIII fragment into the vector containing the HindIII-XbaI fragment. The resulting construct was transfected into COS cells using DEAE-dextran as described in Aruffo et al., 1990, Cell 61:1303–1313). Transfectants were stained with CD40-Ig (25 $\mu$g/ml in DMEM media) followed by FITC-conjugated goat anti-human IgG Fc antibody (1:50 dilution in DMEM, TAGO, Burlingame, Calif.) and visualized by immunofluorescence microscopy. The complete human gp39 was obtained by colony hybridization as described (Sambrook et al., 1989, "Molecular Cloning: A Laboratory Manual", Cold Spring Harbor Laboratory Press, Cold Spring Harbor, N.Y.). The subcloned HindIII-HindIII fragment of the PCR product was used to generate a $^{32}$P-labeled probe by random primed polymerization. Plasmid DNA from three individual clones were transfected into COS cells and cells were stained with CD40-Ig. One clone, clone 19, was positive by this criteria and was used in the remainder of the study. The sequence was determined by dideoxy sequencing using Sequenase™ (United States Biochemical Co., Cleveland, Ohio)

6.2. Results

A cDNA encoding the human gp39 was amplified from a cDNA library prepared from mRNA isolated from PHA activated human peripheral blood T cells by the polymerase chain reaction (PCR) using synthetic oligonucleotides based on the murine gp39 sequence (Armitage et al., 1992, Nature 357:80–82). The PCR product was subcloned into the expression vector CDM8 (Seed, 1987, Nature 329:840–842). COS cells transfected with the CDM8-gp39 plasmid produced protein which bound to CD40-Ig (Noelle et al., 1992, Proc. Natl. Acad. Sci. U.S.A. 89:6550–6554). A complete human gp39 gene was isolated by colony hybridization from the same cDNA library that was used for the PCR amplification of gp39 using the subcloned PCR product as a probe. A number of positive clones were isolated and analyzed by restriction enzyme digestion. DNA corresponding to those clones containing the largest inserts, 1.8–1.5 kb, were transfected into COS cells and their ability to direct the expression of a CD40-Ig binding protein examined. One such clone was positive by this criteria and was analyzed further and is referred TO hereafter as human gp39. Immunoprecipitation of cDNA-encoded human gp39 protein from transfected COS cells using CD40-Ig showed a single band corresponding to a molecular mass of about 32–33 kDa. The COS-cell derived protein is smaller than we had expected based on our previous studies of murine gp39, however, we have observed in many instances that the apparent molecular masses of a number of different T cell surface proteins obtained from COS cell transfectants are smaller than those obtained from T cells (Aruffo and Seed, 1987, EMBO J. 11:3313–3316; Aruffo et al., 1991, J. Exp. Med. 174:949–952). These differences in size may be the result of incomplete glycosylation of the proteins by COS cells.

The human gp39 cDNA is about 1.8 kb in length and encodes a polypeptide of 261 amino acids (aa) with a predicted molecular mass of about 29 kDa consisting of a 22 amino acid amino-terminal cytoplasmic domain, a 24 amino acid hydrophobic transmembrane domain and a 215 amino acid carboxyterminal extracellular (EC) domain with one N-linked glycosylation site (Asn-X-Ser/Thr) in the EC and one in the cytoplasmic domain (nucleotide sequences corresponding to coding sequence and the predicted amino acid sequence are shown in FIG. 1a). The expected orientation of the protein, with an extracellular carboxy-terminus, classifies it as a type II membrane protein and the difference between the predicted and observed molecular mass suggest that it undergoes posttranslational modifications, most likely the addition of carbohydrate groups.

The predicted amino acid sequence of human gp39 was compared with those in the National Biomedical Research Foundation (NBRF) database using the FASTP algorithm and found to have significant homology with tumor necrosis factor (TNF) α (Gray et al., 1984, Nature 312:721–724) and β (Pennica et al., 1984, Nature 312:724–729; Wang et al., 1985, Science 228:149–154) (FIG. 1b). The extracellular domain of gp39 is as closely related to TNF α and β, having about 25% homology with each, just as TNF α and TNF β share about 30% homology (Pennica et al., 1984, Nature 312:724–729).

6.3. Discussion

The ability of the surface receptor CD40 to deliver signals to the B cell has been established using monoclonal antibodies (Clark and Ledbetter, 1986, Proc. Natl. Acad. Sci. 83:4494–4498; Gordon et al., 1987, Eur. J. Immunol. 17:1535–1538). To further study the role of CD40, a cDNA encoding the CD40 ligand from a human source has been isolated and characterized.

Isolation of a cDNA clone encoding human gp39 showed that this type II membrane protein is closely related to TNF a (Gray et al., 1984, Nature 312:721–724) and α (Pennica et al., 1984, Nature 312:724–729; Wang et al., 1985, Science 228:149-154). TNF α and β are pleiotropic cytokines that exist predominantly as secreted proteins.

7. EXAMPLE

Expression of a Soluble Form of gp39 with B Cell Co-Stimulatory Activity

7.1. Materials and Methods

7.1.1. Construction, Characterization, and Preparation of a Soluble gp39 Chimera The extracellular domain of the human gp39 was amplified from the cDNA library prepared from mRNA from PHA activated human peripheral blood lymphocytes. The oligonucleotide primers were designed based on sequence information obtained from the PCR product described above and were designed to place a BamHI site at the 5' end of the gene such that the reading frame would be preserved when the chimeric gene was constructed. The oligonucleotides used were 5'- CGA AGC TTG GAT CCG AGG TTG GAC AAG ATA GAA GAT-3' SEQUENCE ID NO. 15 and 5'-CGC TCT AGA TGT TCA GAG TTT GAG TAA GCC-3' SEQUENCE ID NO. 14. The PCR was performed using the Pfu polymerase with the buffer supplied by the manufacturer (Stratagene, La Jolla, Calif.) with the following temperature program: 5 minutes, 95° C.; 2 minutes, 72° C.; 2 minutes, 55° C.; 40 cycles of amplification consisting of 1 minute, 95° C.; 2 minutes, 55° C.; 3 minutes, 72° C.; 10 minutes, 72° C. The PCR product was digested with BamHI and XbaI and subcloned in a vector containing the gene encoding the murine CD8 (Lyt2a) extracellular domain with a BamHI restriction site generated by PCR. Similarly, the gene encoding the extracellular domain of human CD72 was generated by PCR to contain a BamHI restriction site and subcloned in the CD8-containing vector in the same manner.

The ability of COS cells to express and export shgp39 and sCD72 was tested. First, COS cells were transfected using DEAE-dextran. One day after transfection, cells were trypsinized and replated. One day later, cells were fixed with 2% formaldehyde in PBS (20 min., room temp.) and permeabilized with 2% formaldehyde in PBS containing 0.1% Triton X-100. (20 min., room temp.). Cells transfected with sgp39 were stained with CD40-Ig (25 μg/ml in DMEM, 30 min., room temp.) followed by FITC-conjugated goat anti-human Fc antibody (TAGO, Burlingame, Calif.) diluted 1:500 in DMEM. Cells transfected with sCD72 were stained with the anti-CD72 antibody BU40 (The Binding Site, Birmingham, UK) followed by FITC-conjugated goat anti-mouse Fc antibody (TAGO, Burlingame, Calif.) diluted 1:500 in DMEM.

COS cells transfected with the shgp39 or sCD72 constructs or vector alone (mock) were grown overnight in Cys- and Met- free DMEM to which [$^{35}$S]-L-methionine and [$^{35}$S]-L-cysteine had been added (Tran[$^{35}$S]-label, ICN, Costa Mesa, Calif., 27 μCi/ml). Supernatants were harvested and centrifuged at 1 krpm for 10 minutes. Fusion proteins were recovered from the supernatant using CD40-Ig, 53-6 (anti-murine CD8) plus goat anti-rat Fc, BU40, BU41 (The Binding Site, Birmingham, UK) plus goat anti-mouse IgM Fc, or J3.101 (AMAC Inc., Westbrook, Me.). Goat antibodies were purchased from Organon Teknika Co., West Chester, Pa. For each sample, 1 ml of supernatant, 75 μl Protein A-sepharose (Repligen, Cambridge, Mass.) and the precipitating agent(s) were mixed and incubated at 40° C. for 2 hr. The sepharose was washed extensively with PBS containing 0.01% NP-40 and resuspended in loading buffer containing 5% β-mercaptoethanol. Proteins were subjected to SDS-PAGE in a 8% polyacrylamide gel. The gel was fixed, dried and exposed to film. COS cell supernatants containing shgp39 or sCD72 were generated by transfection of COS cells. One day after transfection, cell media was changed to DMEM containing 2% FBS. Supernatants were harvested eight days after transfection.

7.1.2. Binding Assays

The binding of hgp39 and CD40 to the soluble forms of their respective ligands was tested by staining of transfected COS cells. COS cells were transfected with CD40, hgp39 or vector alone (mock) using DEAE-dextran. One day after transfection, cells were trypsinized and replated. Cells were stained on the following day. Cells expressing gp39 or mock transfected cells were stained with CD40-Ig (25 μg/ml) followed by FITC-conjugated goat and-human Fc. Cells expressing CD40 were stained by incubation with COS cell supernatants containing shgp39 followed by mAb 53-6 (anti-murine CD8, 2.5 μg/ml) then FITC-conjugated goat anti-rat Fc (Organon Teknika Co., West Chester, Pa., 1.5 μg/ml). As controls, COS cells expressing CD40 were stained with FITC-conjugated G28-5 (anti-CD40) or using COS cell supernatants containing sCD72. All incubations were done at room temperature in PBS containing 1 mM CaCl$_2$, 1 mM MgCl$_2$ and 2% FBS and the same buffer was used for all washes. Following staining, cells were fixed with 1% paraformaldehyde in PBS.

The binding of shgp39 to CD40-Ig was investigated in an ELISA assay. Wells of a 96-well plate (Immunolon-2, Dynatech) were coated with 53-6 antibody (anti-murine CD8, 10 μg/ml, 100 μl/well, 50 mM sodium bicarbonate, pH 9.6, 1 hour, room temperature). Wells were washed with phosphate buffered saline containing 0.05% Tween-20 (TPBS) and blocked with 1X Specimen Diluent Concentrate (Genetic Systems, 225 μl/well, 2 hours, room temperature). Wells were washed (TPBS). Supernatants from COS cells expressing either sgp39 or sCD72 were added (150 μl/well) and plates were incubated at 4° C. overnight. Wells were washed (TPBS) and fusion proteins CD40-Ig or Leu8-Ig were added (serially diluted in PBS containing 1 mM $CaCl_2$ and 1 mM $MgCl_2$, 20 μg/ml to 0.6 μg/ml, 100 μl/well, 1 hr., room temp.) Wells were washed (TPBS) and peroxidase-conjugated goat F(ab')2 anti-human IgG was added to each well (TAGO, Burlingame Calif., 1:5000 dilution in 1X Specimen Diluent, 100 μl/well, 1 hr., room temp.) Wells were washed (TPBS) and chromogenic substrate was added (Genetic Systems chromogen diluted 1:100 in EIA Buffered Substrate, Genetic Systems, 100 μl/well). The reaction was stopped after 10 minutes with the addition of Stop Buffer (Genetic Systems, 100 μl/well) and the absorbance was measured on an ELISA reader at dual wavelengths, namely 450 or 630nm. Additionally, the ELISA was performed by immobilization of CD40Ig on plates coated with goat anti-human Fc. Binding of shgp39 from increasing dilutions of COS cell supernatants was detected using 53-6 Mab followed by FITC conjugated goat anti-rat Fc. Fluorescence was measured on a microplate reader.

7.1.3. B Cell Proliferation Assays

Peripheral blood mononuclear cells (PBMC) were isolated by centrifugation through Lymphocyte Separation Medium (Litton Bionetics, Kensington, Md.). Human B lymphocytes were enriched from PBMC by passage of cells over nylon columns (Wako Chemicals USA, Inc., Richmond, Va.) and harvesting of adherent cells. These cells were then treated with leu-leu methyl ester (Sigma, St. Louis, Mo.) to deplete monocytes and NK cells. The resulting cell population was analyzed by flow cytometry on an EPICS C (Coulter Electronics, Hileah, Fla.) and consisted of 50% human peripheral B cells.

Tonsillar B cells were prepared from intact tonsils by mincing to give a tonsillar cell suspension. The cells were then centrifuged through Lymphocyte Separation Medium, washed twice and fractionated on a discontinuous Percoll (Sigma, St. Louis, Mo.) gradient. Cells with a density greater than 50% were collected, washed twice and used in proliferation assays.

COS cells transfected with the gp39 construct or vector alone (mock-COS) were harvested from tissue culture plates with EDTA, washed twice with PBS, suspended at $5 \times 10^6$ cells/ml and irradiated with 5000 rads from a 137 Cs source. COS cells were used at a ratio of 1:4 ($1 \times 10^4$ COS cells vs. $4 \times 10^4$ B cells) in proliferation assays.

Measurement of proliferation was performed by culturing cells in quadruplicate samples in flat-bottomed 96-well microtiter plates at $5 \times 10^4$ cells per well in complete RPMI medium containing 10% FCS. Reagents used were 1F5 (anti-CD20, 1 μg/ml); PMA (10 ng/ml, LC Services Woburn, Mass.); G28-5 (anti-CD40, 1 μg/ml); CD40Ig (5 μg/ml in assays of peripheral blood B cells, 20 μg/ml in assays of tonsilar B cells); supernatants of COS cells expressing shgp39 or sCD72 (diluted 1:4). Cell proliferation was measured by uptake of [$^3$H]thymidine (6.7 Ci/mmol; New England Nuclear, Boston, Mass.) after 5 days of culture and an overnight pulse. Cells were harvested onto glass fiber filters and radioactivity was measured in a liquid scintillation counter.

7.2. Results

Figure 2B:
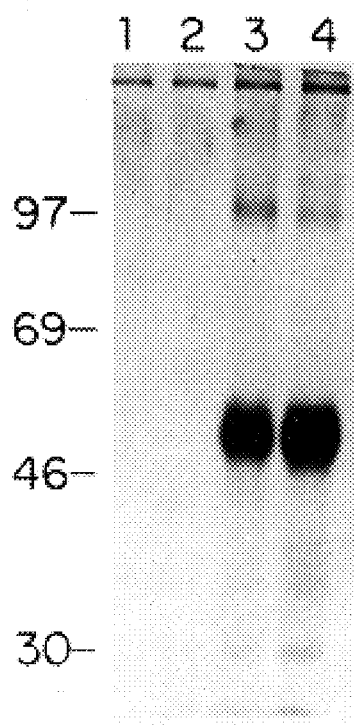

7.2.1. Preparation and Characterization of the Recombinant gp39 as a Chimeric Fusion Protein Because gp39 is a type II membrane protein, and type II membrane proteins are oriented with a carboxyterminal EC domain, a fusion construct was designed such that a tag polypeptide was placed amino-terminal to the EC portion of the protein, replacing the transmembrane and cytoplasmic domains of the surface protein. The tag polypeptide should contain an amino-terminal secretory signal sequence to allow export of the fusion protein. We chose the murine CD8 EC domain (Nakauchi et al., 1985, Proc. Natl. Acad. Sci. U.S.A. 82:5126–5130) as our tag polypeptide to construct our fusion proteins of type II membrane proteins for four reasons: (i) the use of an intact extracellular protein domain with a well defined tertiary structure as the tag polypeptide minimizes the chances that the tag polypeptide will affect the tertiary structure of the surface protein to which it is fused while maximizing the likelihood that the fusion protein will be expressed and exported, (ii) a previously studied CD8 Ig chimera demonstrated that CD8 fusion proteins are produced and exported by COS cells in high yield, (iii) a large number of mAb directed to CD8 are available and can be used to manipulate the recombinant CD8 fusion proteins; and (iv) the interaction between murine CD8 and human MHC I is not detectable. To generate the CD8-gp39 fusion gene, shgp39, a cDNA fragment encoding the EC domain of murine CD8 was fused with a cDNA fragment encoding the EC domain of gp39 as described in the Materials and Methods (FIG. 2a). The shgp39 protein was prepared by transient expression in COS cells and recovered from COS cell supernatants with anti-CD8 mAb or with a soluble recombinant CD40-Ig chimera which we used in our earlier murine gp39 studies (FIG. 2b). The shgp39 protein has a molecular mass of about 50 kDa (FIG. 2b) when analyzed by SDS-PAGE under reducing conditions. Experimental results indicate that shgp39 forms dimers and trimers in solution.

Figure 2C:
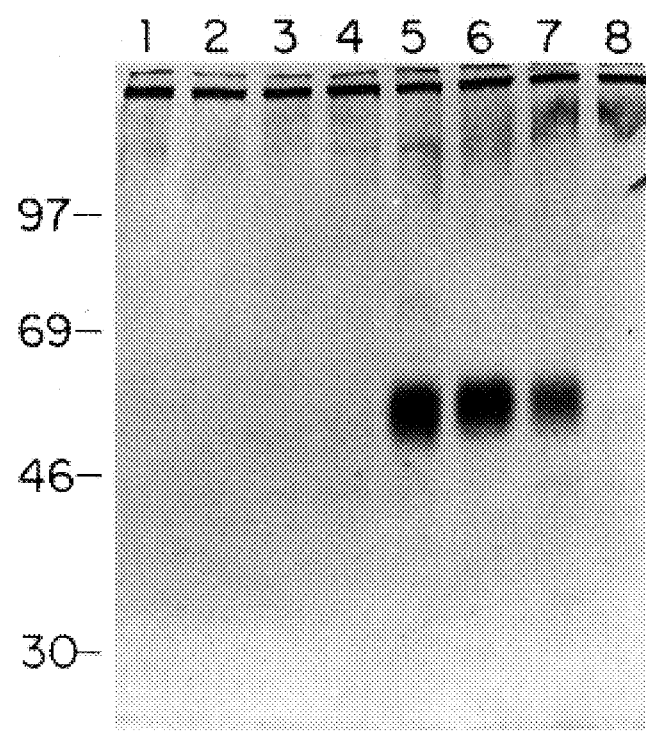

As a control, a chimeric gene encoding a soluble recombinant form of the B cell antigen CD72 (Von Hoegen et al., 1990, J. Immunol. 144:4870–4877), another type II membrane protein, was constructed (FIG. 2a). The sCD72 protein was also produced by transient expression in COS cells and recovered from COS cell supernatants with anti-CD8 mAb or with three anti-CD72 mAb tested, but not with the CD40-Ig fusion protein (FIG. 2c).

To further characterize the interaction between CD40 and the soluble recombinant hgp39, COS cells were transfected with a cDNA encoding the full length CD40 protein (Stamenkovic et al. 1989, EMBO J. 8:1403–1410) and their ability to bind to shgp39, sCD72, and anti-CD40 mAb examined by fluorescence microscopy. Both the shgp39 and the anti-CD40 mAb bound to the transfectants while sCD72 did not (FIG. 3). In addition, COS cells were transfected with a cDNA encoding the surface bound gp39 and their ability to bind to CD40-Ig (Noelle et al., 1992, Proc. Natl. Acad. Sci. U.S.A. 89:6550–6554)) or an irrelevant Ig fusion protein, Leu8-Ig (Aruffo et al. 1992, Proc. Natl. Acad. Sci. U.S.A. 89:2292–2296), examined. CD40-Ig, but not Leu8-Ig, bound to gp39 expressing COS cells (FIG. 3). In parallel experiments, shgp39 and CD72 were immobilized in the wells of a 96 well microtiter dish via an anti-CD8 mAb and their binding to increasing concentrations of CD40-Ig or a control immunoglobulin fusion protein, Leu8-1g; examined. The binding of CD40-Ig to immobilized shgp39 was saturable, while CD40-Ig did not bind to sCD72 and Leu8-Ig did not bind to shgp39 (FIG. 4).

7.2.2. Human gp39 Requires a Co-Stimulus to Induce B Cell Proliferation

To examine the role of gp39-CD40 interactions in B cell activation, COS cells transfected with either the cDNA encoding hgp39 or vector alone (mock) were tested for their ability to stimulate B cell proliferation. Resting, peripheral blood B cells proliferated only weakly when incubated with hgp39-expressing COS cells alone (FIG. 5). However, upon exposure to hgp39-expressing COS cells in conjunction with either (i) lF5 mAb (Clark et al., 1985, Proc. Natl. Acad. Sci. U.S.A. 82:1766–1770), directed against the B cell surface protein CD20, or (ii) PMA, vigorous B cell proliferation was observed. In both cases, the hgp39driven B cell proliferation could be reduced to background levels with the soluble CD40-Ig fusion protein (FIG. 5). B cells proliferated weakly when incubated with mock transfected COS cells in the presence of either the anti-CD20 mAb or PMA and this proliferation was unaffected by the presence of CD40-Ig (FIG. 5). The weak B cell proliferation observed with hgp39-expressing COS cells in the absence of a co-stimulatory signal suggests that in this case COS cells also provide co-stimulatory signals that synergize with CD40 signals to drive B cell proliferation.

Resting, human peripheral blood B cells were incubated with the soluble recombinant hgp39, shgp39, or a control soluble fusion protein, sCD72, in the absence or presence of anti-CD20 mAb or PMA. Although very weak proliferation was observed with shgp39 alone, shgp39 induced vigorous B cell proliferation when either anti-CD20 mAb or PMA was present (FIG. 6). B cell proliferation was not observed with sCD72, anti-CD20 mAb or PMA alone or with sCD72 in conjunction with anti-CD20 mAb or PMA (FIG. 6).

Figure 7A:
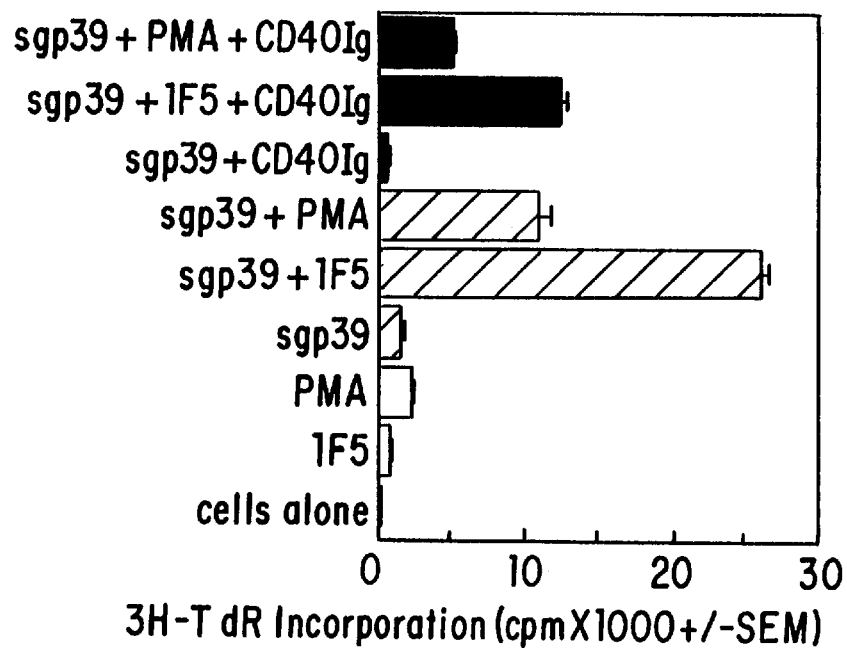
Figure 7B:
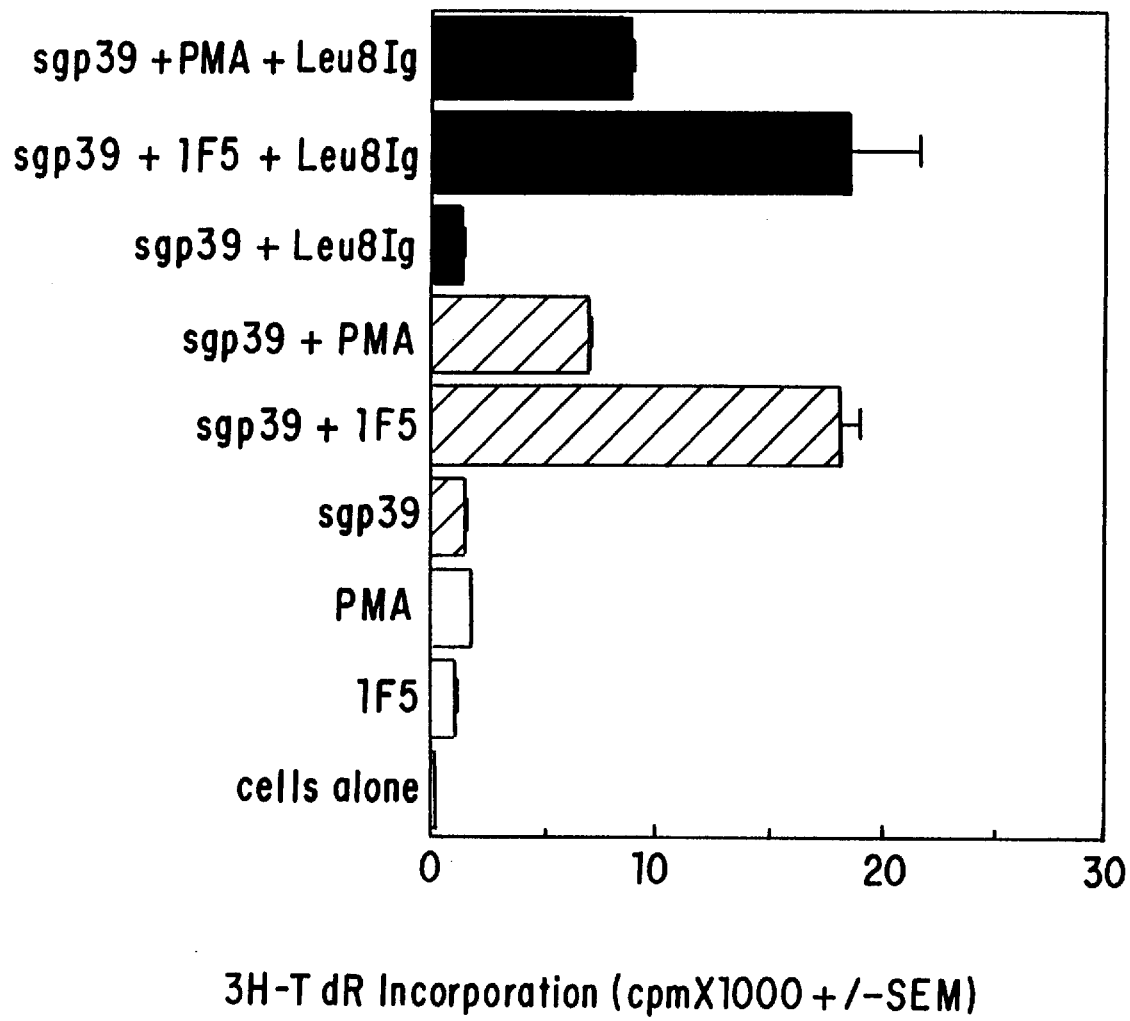

In parallel experiments resting, dense human tonsillar B cells were prepared as described in the Materials and Methods section and their ability to proliferate in response to shgp39 and sCD72 examined (FIG. 7). As had been seen with peripheral blood B cells, tonsillar B cells proliferated weakly in response to shgp39 but showed strong proliferation when incubated with shgp39 in the presence of the anti-CD20 mAb IF5 or PMA. No significant proliferation over background levels was observed when the cells were incubated with sCD72 alone or in the presence of the 1F5 mAb or PMA. To examine the specificity of the shgp39 driven activation response the ability of CD40-Ig to block the shgp39/IF5 or shgp39/PMA driven B cell proliferation was examined. CD40-Ig was able to reduce the shgp39 driven B cell activation (~20 μg/ml gave ~50% inhibition, FIG. 7A) while a control fusion protein Leu-8-Ig had no effect (FIG. 7B).

7.3. Discussion

It has been reported that purified murine splenic B cells and human tonsillar B cells proliferate when incubated with CV1/EBNA cells expressing murine gp39 in the absence of co-stimulus (Armitage et al., 1992, Nature 357:80–82). Based on these data it had been thought that gp39 is directly mitogenic for B cells. To determine if gp39 binding to CD40 is able to stimulate resting B cells to proliferate in the absence of other co-stimulatory signals, and the effect of the fibroblast cells in the stimulation, the proliferation of B cells in response to COS cells expressing full length hgp39 or shgp39 was tested. In contrast to the teachings of Armitage, supra, which suggest that gp39 must be associated with a membrane to be active, our results show that the hgp39 was active in both membrane-associated and soluble forms; however, interesting differences between hgp39+ COS cells and shgp39 were seen. COS cells expressing hgp39 were able to induce only weak B cell proliferation in the absence of co-stimuli but could synergize with co-stimuli such as anti-CD20 mAb or PMA to induce vigorous B cell proliferation. In all cases, the B cell proliferation could be reduced to background levels with soluble recombinant hgp39 receptor, CD40-Ig.

sHgp39 was only able to induce resting B cells, isolated from either peripheral blood or tonsils, to proliferate in conjunction with co-stimuli such as anti-CD20 mAb or PMA. As had been observed with hgp39-expressing COS cells, shgp39 driven B cell activation could be inhibited with CD40-Ig but not with an irrelevant Ig fusion protein.

These data indicate that hgp39 requires a co-stimulatory signal to most effectively drive B cell proliferation and that there is no strict requirement for cell surface expression of hgp39 for activity. In addition, the ability of hgp39 expressed on the surface of COS cells to stimulate weak B cell proliferation supports the idea that COS cells may also provide low level co-stimulatory signals, as yet undefined, that can synergize with those provided by hgp39.

The development of factor dependent, long term B cell cultures has important applications for the study of B cell growth and differentiation and the development of antigen-specific B cell lines (Tisch et al., 1988, Immunol. Today 9:145–150). Experiments with anti-CD40 mAb showed that CD40 signals can synergize with other co-stimulatory signals such as those delivered by anti-CD20 mAb to drive B cell proliferation and that treatment of B cells with anti-CD40 mAb induces a state of B cell "alertness" which allows them to respond more readily to subsequent activation signals. The ability of shgp39 to stimulate B cell proliferation in conjunction with anti-CD20 mAb or PMA suggests that it may be used to create in vitro systems for long term B cell growth.

It is interesting to note that the CD40-Ig fusion protein and the shgp39 fusion described here can be used to, respectively, either inhibit or stimulate the CD40 response in B cells and thus are useful tools in the study of B-cell/T cell interactions and in clinical applications.

8. Deposit of Microorganisms

The following were deposited on Aug. 14, 1992 with the American Type Culture Collection, 10801 University Boulevard, Manassas, Va. 20110-2209:

|  | ATCC Designation |
|---|---|
| *Escherichia coli* CDM7B⁻ MC1061/p3-shgp39 | 69049 |
| *Escherichia coli* CDM8 MC1061/p3-hgp39 | 69050 |

The present invention is not to be limited in scope by the microorganisms deposited since the deposited embodiments are intended as illustrations of single aspects of the invention and any microorganisms which are functionally equivalent are within the scope of the invention.

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those skilled in the art from the foregoing description and accompanying drawings. Such modifications are intended to fall within the scope of the appended claims.

It is also to be understood that all base pair sizes given for nucleotides are approximate and are used for purposes of description.

Various publications have been cited herein, the contents of which are hereby incorporated by reference in their entirety.

---

What is claimed is:

1. A fusion protein comprising a sequence as set forth in FIG. 1A (SEQ ID NO: 2) from amino acid residues 47 to 261 attached to the extracellular domain of the CD8 protein.

2. The fusion protein of the claim 1 as produced by expression of plasmid CDM7B⁻/p3-shgp39, as deposited with the American Type Culture Collection and assigned Accession Number 69049.

* * * * *